United States Patent
Choo et al.

(10) Patent No.: US 7,080,330 B1
(45) Date of Patent: Jul. 18, 2006

(54) CONCURRENT MEASUREMENT OF CRITICAL DIMENSION AND OVERLAY IN SEMICONDUCTOR MANUFACTURING

(75) Inventors: Bryan Choo, Mountain View, CA (US); Bharath Rangarajan, Santa Clara, CA (US); Bhanwar Singh, Morgan Hill, CA (US); Carmen Morales, San Jose, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 433 days.

(21) Appl. No.: 10/379,738

(22) Filed: Mar. 5, 2003

(51) Int. Cl.
*G06F 17/50* (2006.01)
(52) U.S. Cl. .................. 716/4; 716/19; 716/21
(58) Field of Classification Search .................... 716/4, 716/19, 20, 21
See application file for complete search history.

(56) References Cited

U.S. PATENT DOCUMENTS 5,042,009 A * 8/1991 Kazerounian et al. . 365/185.18
6,650,424 B1 * 11/2003 Brill et al. .................. 356/601
2002/0018217 A1 * 2/2002 Weber-Grabau et al. .... 356/601
2002/0158193 A1 * 10/2002 Sezginer et al. ........ 250/237 G

OTHER PUBLICATIONS

Kynett et al.,"A in-system reprogrammable 32 K×8 CMOS Flash Memory", Oct. 1988, IEEE Jpurnal of Solid-State Circuits, vol. 23, iss. 5, pp. 1157-1163.*

* cited by examiner

*Primary Examiner*—Sun James Lin
(74) *Attorney, Agent, or Firm*—Amin & Turocy, LLP

(57) ABSTRACT

A system and methodology are disclosed for monitoring and controlling a semiconductor fabrication process. One or more structures formed on a wafer matriculating through the process facilitate concurrent measurement of critical dimensions and overlay via scatterometry or a scanning electron microscope (SEM). The concurrent measurements mitigate fabrication inefficiencies, thereby reducing time and real estate required for the fabrication process. The measurements can be utilized to generate feedback and/or feed-forward data to selectively control one or more fabrication components and/or operating parameters associated therewith to achieve desired critical dimensions and to mitigate overlay error.

25 Claims, 18 Drawing Sheets

CONCURRENT MEASUREMENT OF CRITICAL DIMENSION AND OVERLAY IN SEMICONDUCTOR MANUFACTURING

TECHNICAL FIELD

The present invention generally relates to monitoring and/or controlling a semiconductor fabrication process, and in particular to a system and methodology for concurrently measuring critical dimensions and overlay during the fabrication process and controlling operating parameters to refine the process in response to the measurements.

BACKGROUND

In the semiconductor industry, there is a continuing trend toward higher device densities. To achieve these high densities, there has been and continues to be efforts toward scaling down device dimensions (e.g., at submicron levels) on semiconductor wafers. In order to accomplish such high device packing density, smaller and smaller feature sizes are required in integrated circuits (ICs) fabricated on small rectangular portions of the wafer, commonly known as dies. This may include the width and spacing of interconnecting lines, spacing and diameter of contact holes, the surface geometry such as corners and edges of various features as well as the surface geometry of other features. To scale down device dimensions, more precise control of fabrication processes are required. The dimensions of and between features can be referred to as critical dimensions (CDs). Reducing CDs, and reproducing more accurate CDs facilitates achieving higher device densities through scaled down device dimensions and increased packing densities.

The process of manufacturing semiconductors or ICs typically includes numerous steps (e.g., exposing, baking, developing), during which hundreds of copies of an integrated circuit may be formed on a single wafer, and more particularly on each die of a wafer. In many of these steps, material is overlayed or removed from existing layers at specific locations to form desired elements of the integrated circuit. Generally, the manufacturing process involves creating several patterned layers on and into a substrate that ultimately forms the complete integrated circuit. This layering process creates electrically active regions in and on the semiconductor wafer surface. The layer to layer alignment and isolation of such electrically active regions depends, at least in part, on the precision with which features can be placed on a wafer. If the layers are not aligned within acceptable tolerances, overlay errors can occur compromising the performance of the electrically active regions and adversely affecting chip reliability.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its purpose is merely to present some concepts of the invention in a simplified form as a prelude to the more detailed description that is presented later.

According to one or more aspects of the present invention, one or more structures formed on a wafer matriculating through a semiconductor fabrication process facilitate concurrent measurement of overlay and one or more critical dimensions in the fabrication process with either scatterometry or a scanning electron microscope (SEM). The concurrent measurements mitigate fabrication inefficiencies as two operations are combined into one. The combined measurements facilitate a reduction in, among other things, time and real estate required for the fabrication process. The measurements can be utilized to generate control data that can be fed forward and/or backward to selectively adjust one or more fabrication components and/or operating parameters associated therewith to bring critical dimensions within acceptable tolerances and to mitigate overlay errors.

To the accomplishment of the foregoing and related ends, certain illustrative aspects of the invention are described herein in connection with the following description and the annexed drawings. These aspects are indicative, however, of but a few of the various ways in which one or more of the principles of the invention may be employed and the present invention is intended to include all such aspects and their equivalents. Other advantages and novel features of the invention will become apparent from the following detailed description of the invention when considered in conjunction with the drawings.

DETAILED DESCRIPTION OF THE INVENTION

Figure 1:
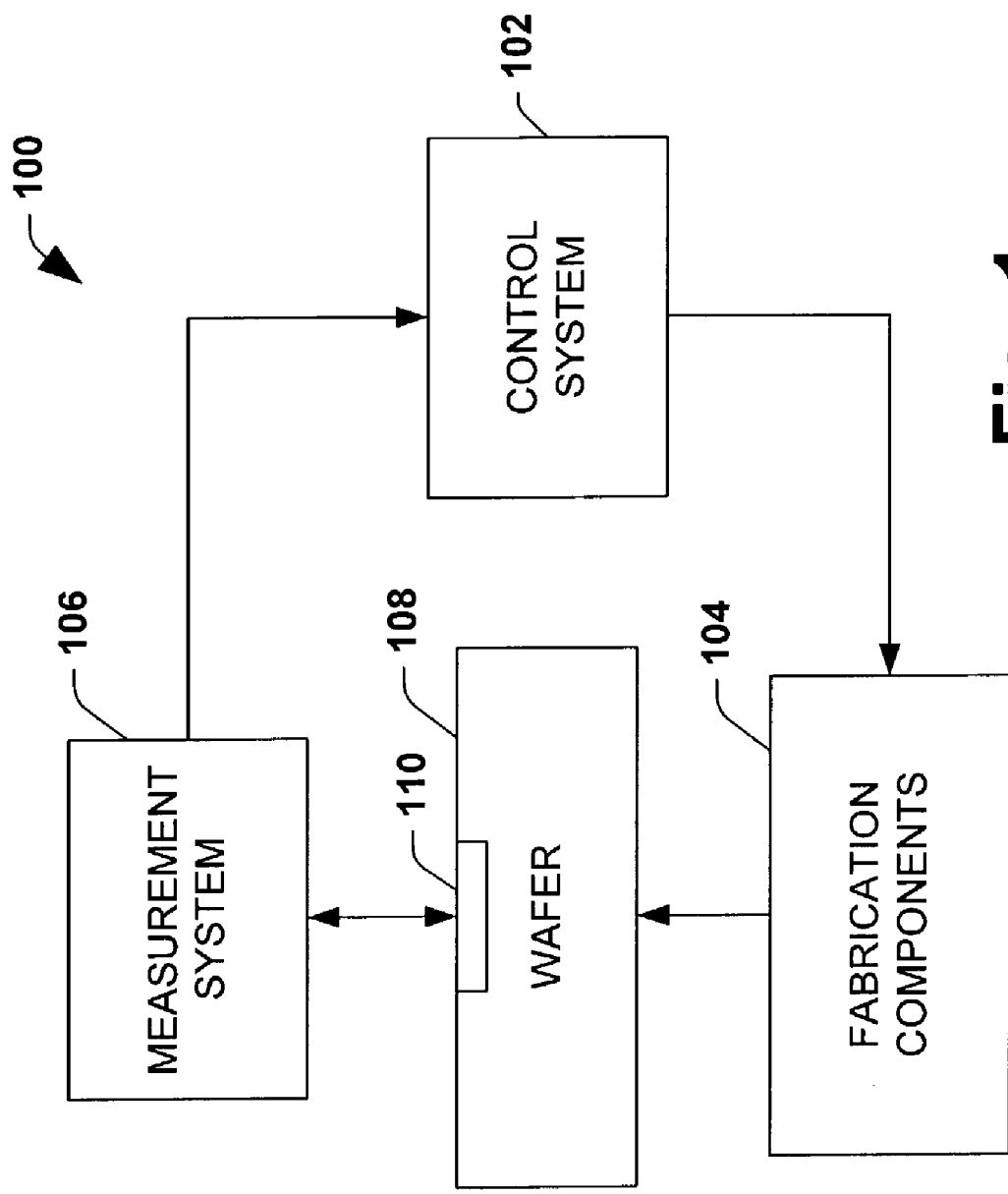
FIG. 1 is a block diagram schematically illustrating at a high level a system for monitoring and controlling a semiconductor fabrication process in accordance with one or more aspects of the present invention.

The present invention is now described with reference to the drawings, wherein like reference numerals are used to refer to like elements throughout. In the following description, for purposes of explanation, numerous specific details are set forth in order to provide a thorough understanding of the present invention. It may be evident, however, to one skilled in the art that one or more aspects of the present invention may be practiced with a lesser degree of these specific details. In other instances, well-known structures and devices are shown in block diagram form in order to facilitate describing one or more aspects of the present invention.

The term "component" as used herein includes computer-related entities, either hardware, a combination of hardware and software, software, or software in execution. For example, a component may be a process running on a processor, a processor, an object, an executable, a thread of execution, a program and a computer. By way of illustration, both an application running on a server and the server can be components. By way of further illustration, both a stepper and a process controlling the stepper can be components.

It is to be appreciated that various aspects of the present invention may employ technologies associated with facilitating unconstrained optimization and/or minimization of error costs. Thus, non-linear training systems/methodologies (e.g., back propagation, Bayesian, fuzzy sets, non-linear regression, or other neural networking paradigms including mixture of experts, cerebella model arithmetic computer (CMACS), radial basis functions, directed search networks and function link networks) may be employed.

FIG. 1 illustrates a system 100 for monitoring and controlling an integrated circuit (IC) fabrication process according to one or more aspects of the present invention. The system 100 includes a control system 102, fabrication components 104 of the process, a measurement system 106 and a wafer 108 undergoing the fabrication process. The wafer 108 has one or more structures 110 formed therein according to one or more aspects of the present invention. The control system 102 is operatively coupled to the measurement system 106 and the fabrication components 104 and selectively controls of the fabrication components 104 and/or one or more operating parameters associated therewith (e.g., via feed forward and/or feedback) based upon readings taken by the measurement system 106. The measurement system 106 includes either a scatterometry system or a scanning electron microscope (SEM) system (not shown) which interacts with the structure 110 to concurrently measure critical dimensions and overlay. These concurrent measurements can be utilized to monitor and control the fabrication process while mitigating the amount of test equipment, real estate and time required for the fabrication process. The measurements can, in particular, be utilized for generating feedback and/or feed-forward data for mitigating overlay and/or bringing critical dimensions within acceptable tolerances.

It is to be appreciated that any of a variety of fabrication components and/or operating parameters associated therewith can be selectively controlled based upon the readings taken by the measurement system 106. By way of example and not limitation, this can include, but is not limited to, temperatures associated with the process, pressures associated with the process, concentration of gases and chemicals within the process, composition of gases, chemicals and/or other ingredients within the process, flow rates of gases, chemicals and/or other ingredients within the process, timing parameters associated with the process and excitation voltages associated with the process. By way of further example, parameters associated with high-resolution photolithographic components utilized to develop IC's with small closely spaced apart features can be controlled to mitigate overlay errors and achieve desired critical dimensions. In general, lithography refers to processes for pattern transfer between various media and in semiconductor fabrication, a silicon slice, the wafer, is coated uniformly with a radiation-sensitive film, the photoresist. The photoresist coated substrate is baked to evaporate any solvent in the photoresist composition and to fix the photoresist coating onto the substrate. An exposing source (such as light, x-rays, or an electron beam) illuminates selected areas of the surface of the film through an intervening master template for a particular pattern. The lithographic coating is generally a radiation-sensitized coating suitable for receiving a projected image of the subject pattern. Once the image from the intervening master template is projected onto the photoresist, it is indelibly formed therein.

Light projected onto the photoresist layer during photolithography changes properties (e.g., solubility) of the layer such that different portions thereof (e.g., the illuminated or un-illuminated portions, depending upon the photoresist type) can be manipulated in subsequent processing steps. For example, regions of a negative photoresist become insoluble when illuminated by an exposure source such that the application of a solvent to the photoresist during a subsequent development stage removes only non-illuminated regions of the photoresist. The pattern formed in the negative photoresist layer is, thus, the negative of the pattern defined by opaque regions of the template. By contrast, in a positive photoresist, illuminated regions of the photoresist become soluble and are removed via application of a solvent during development. Thus, the pattern formed in the positive photoresist is a positive image of opaque regions on the template. Controlling the degree to which a photoresist is exposed to illumination (e.g., time, intensity) can thus affect the fidelity of pattern transfer and resulting critical dimensions and overlay. For example, overexposure can create features that are too thin, resulting in spaces which are larger than desired, while underexposure can create features that are too wide, resulting in spaces which are smaller than desired.

The type of illumination utilized to transfer the image onto a wafer can also be controlled to affect critical dimensions. For instance, as feature sizes are driven smaller and smaller, limits are approached due to the wavelengths of the optical radiation. As such, that type of radiation and thus the wavelengths of radiation utilized for pattern transfers can be controlled to adjust critical dimensions and mitigate overlay. For instance, radiation having more conducive wavelengths (e.g., extreme ultraviolet (EUV) and deep ultraviolet (DUV) radiation having wavelengths within the range of 5–200 nm) can be utilized for lithographic imaging in an effort to accurately achieve smaller feature sizes. However, such radiation can be highly absorbed by the photoresist material. Consequently, the penetration depth of the radiation into the photoresist can be limited. The limited penetration depth requires use of ultra-thin photoresists so that the radiation can penetrate the entire depth of the photoresist in order to effect patterning thereof. The performance of circuits formed through photolithographic processing is, thus, also affected by the thickness of photoresist layers. The thickness of photoresist layers can be reduced through chemical mechanical polishing (CMP). In general, CMP employs planarization techniques wherein a surface is processed by a polishing pad in the presence of an abrasive or non-abrasive liquid slurry. The slurry employed reacts with the photoresist at the surface/subsurface range. Preferably the degree of reaction is not great enough to cause rapid or measurable dissolution (e.g., chemical etching) of the photoresist, but merely sufficient to cause a minor modification of chemical bonding in the photoresist adequate to facilitate surface layer removal by applied mechanical stress (e.g., via use of a CMP polishing pad). Thus, critical dimensions and overlay can be affected by controlling the concentration, rate of flow and degree of abrasiveness of slurry applied during the CMP process as well as the amount of pressure applied between the polishing pad and water during the process.

Depending upon the resist system utilized, post exposure baking may also be employed to activate chemical reactions in the photoresist to affect image transfer. The temperatures and/or times that portions of the wafer are exposed to particular temperatures can be controlled to regulate the uniformity of photoresist hardening (e.g., by reducing standing wave effects and/or to thermally catalyze chemical reactions that amplify the image). Higher temperatures can cause faster baking and faster hardening, while lower temperatures can cause slower baking and correspondingly slower hardening. The rate and uniformity of photoresist hardening can affect critical dimensions and overlay, such as, for example, by altering the consistency of a line width. Accordingly, time and temperature parameters can be controlled during post exposure baking to affect critical dimensions and overlay.

Operating parameters of an etching stage can similarly be controlled to achieve desired critical dimensions and to mitigate overlay. After illumination, the pattern image is transferred into the wafer from the photoresist coating in an etching stage wherein an etchant, as well as other ingredients, are applied to the surface of the wafer by an excitation voltage or otherwise. The etchant removes or etches away portions of the wafer exposing during the development process. Portions of the wafer under less soluble areas of the photoresist are protected from the etchants. The less soluable portions of the photoresist are those portions that are not affected by the developer during the development process and that are not affected by the etchant during the etching process. These insoluble portions of the photoresist are removed in subsequent processing stage(s) to completely reveal the wafer and the pattern(s) formed therein. The concentration of materials utilized in etching can thus be controlled to achieve desired critical dimensions and to mitigate overlay for instance by affecting the accuracy with which selected portions of the wafer are etched away.

Parameters relating to the type of template utilized to transfer an image onto a wafer can also be controlled to affect critical dimensions, layer to layer alignment and overlay. Where the template is a reticle, the pattern is transferred to only one (or a few) die per exposure, as opposed to where the template is a mask and all (or most) die on the wafer are exposed at once. Multiple exposures through a reticle are often performed in a step and scan fashion. After each exposure, a stage to which the wafer is mounted is moved or stepped to align the next die for exposure through the reticle and the process is repeated. This process may need to be performed as many times as there are die in the wafer. Thus, stepper movement can be controlled to mitigate overlay error (e.g., by feeding fed forward and/or backward measurements to a stepper motor). The pattern formed within the reticle is often an enlargement of the pattern to be transferred onto the wafer. This allows more detailed features to be designed within the reticle. Energy from light passed through the reticle can, however, heat the reticle when the image is exposed onto the wafer. This can cause mechanical distortions in the reticle due to thermal expansion and/or contraction of the reticle. Such distortions may alter the geometry of intricate features (e.g., by narrowing a line) and/or interfere with layer to layer registration to such a degree that a resulting circuit does not operate as planned when the image is transferred onto the wafer. Moreover, since the pattern is usually an enlargement of the pattern to be transferred onto the wafer, it typically has to be reduced (e.g., via a de-magnifying lens system) during the lithographic process. Shrinking an already distorted feature (e.g., a narrowed line) can have a deleterious effect on critical dimensions. Thus, while such a template may be effective to transfer more intricate pattern designs, it calls for highly accurate alignment and imaging to mitigate overlay errors and maintain critical dimensions to within acceptable tolerances. Temperature controls can thus be employed to mitigate thermally induced mechanical distortions in the reticle.

Additionally, parameters relating to film growth or deposition components (e.g., producing metals, oxides, nitrides, poly, oxynitrides or insulators) can be controlled to achieve desired critical dimensions and mitigate overlay. Such films can be formed through thermal oxidation and nitridation of single crystal silicon and polysilicon, the formation of silicides by direct reaction of a deposited metal and the substrate, chemical vapor deposition (CVD), physical vapor deposition (PVD), low pressure CVD (LPCVD), plasma enhanced CVD (PECVD), rapid thermal CVD (RTCVD), metal organic chemical vapor deposition (MOCVD) and pulsed laser deposition (PLD). The rates of flow, temperature, pressures, concentrations and species of materials supplied during the semiconductor fabrication process can thus be controlled to govern film formation which bears on critical dimensions and overlay.

Scatterometry or scanning electron microscope (SEM) techniques can be employed in accordance with one or more aspects of the present invention to concurrently measure critical dimensions and overlay at different points in an IC fabrication process to determine what effect, if any, the various processing components are having on the fabrication process. Different grating and/or feature heights and/or depths may, for example, be measured to generate different signatures that may be indicative of the effect that one or more processing components are having upon the fabrication process and which operating parameters of which processing components, if any, should thus be adjusted to rectify any undesirable processing. The processing components and/or operating parameters thereof can be controlled based upon feedback/feedforward information generated from the measurements. For example, at a first point in time a first signature may be generated that indicates that desired critical dimensions have not yet been achieved but are developing within acceptable tolerances, but that an overlay error is occurring. Thus, the process may be adapted in an attempt to mitigate overlay error, but not affect developing critical dimensions. Then, at a second point in time a second signature may be generated that indicates that an overlay error is no longer occurring, but that the desired critical dimensions still have not been achieved. Thus, the process may be allowed to continue until a later point in time when a corresponding signature indicates that the desired critical dimensions have been achieved without overlay error.

Figure 2:
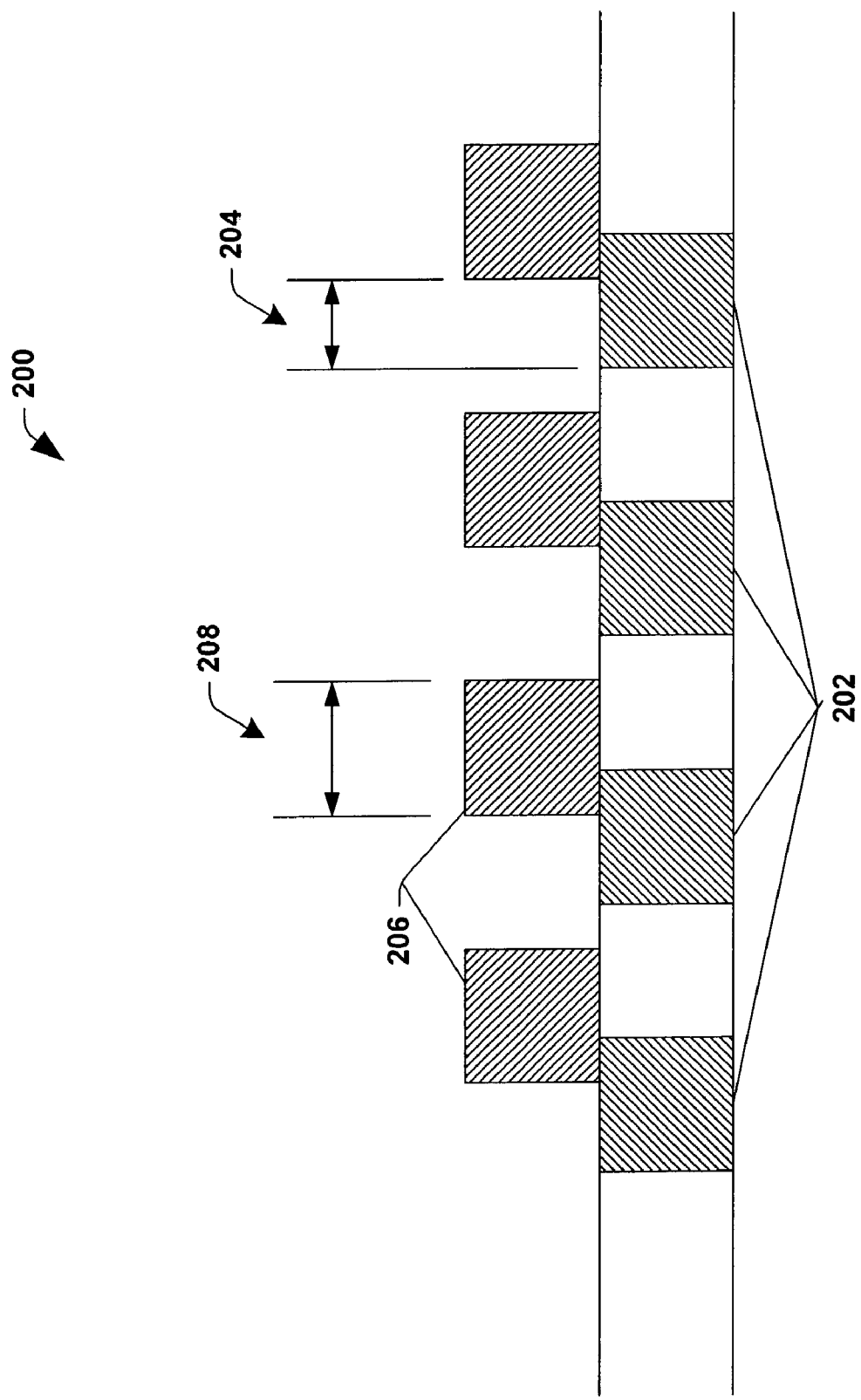
FIG. 2 is a cross sectional side view of a structure in accordance with one or more aspects of the present invention that facilitates concurrent measurement of critical dimensions and overlay with scatterometry.

Turning to FIG. 2, a cross sectional side view of a combined structure 200 in accordance with one or more aspects of the present invention is illustrated. The structure 200 facilitates concurrent measurement of critical dimensions and overlay with a scatterometry system and can be formed on a portion (e.g., a die) of a wafer matriculating through an IC fabrication process, for example. The structure includes one or more underlying gratings 202 that facilitate overlay 204 measurements and alignment with other layers and one or more overlying gratings 206 that facilitate critical dimension 208 measurements. It is to be appreciated that the overlying gratings 206 can be printed at any location on the wafer where it is desired to monitor critical dimensions. Measurements can thus be taken at more appropriate circuit locations, such as at a core memory array, for example, as opposed to test structures in scribe lines. Measuring critical dimensions and overlay in a single operation with a single tool (e.g., by scatterometry) mitigates fabrication duration and spacing requirements. This allows efficiency to be increased without sacrificing quality control.

Figure 3:
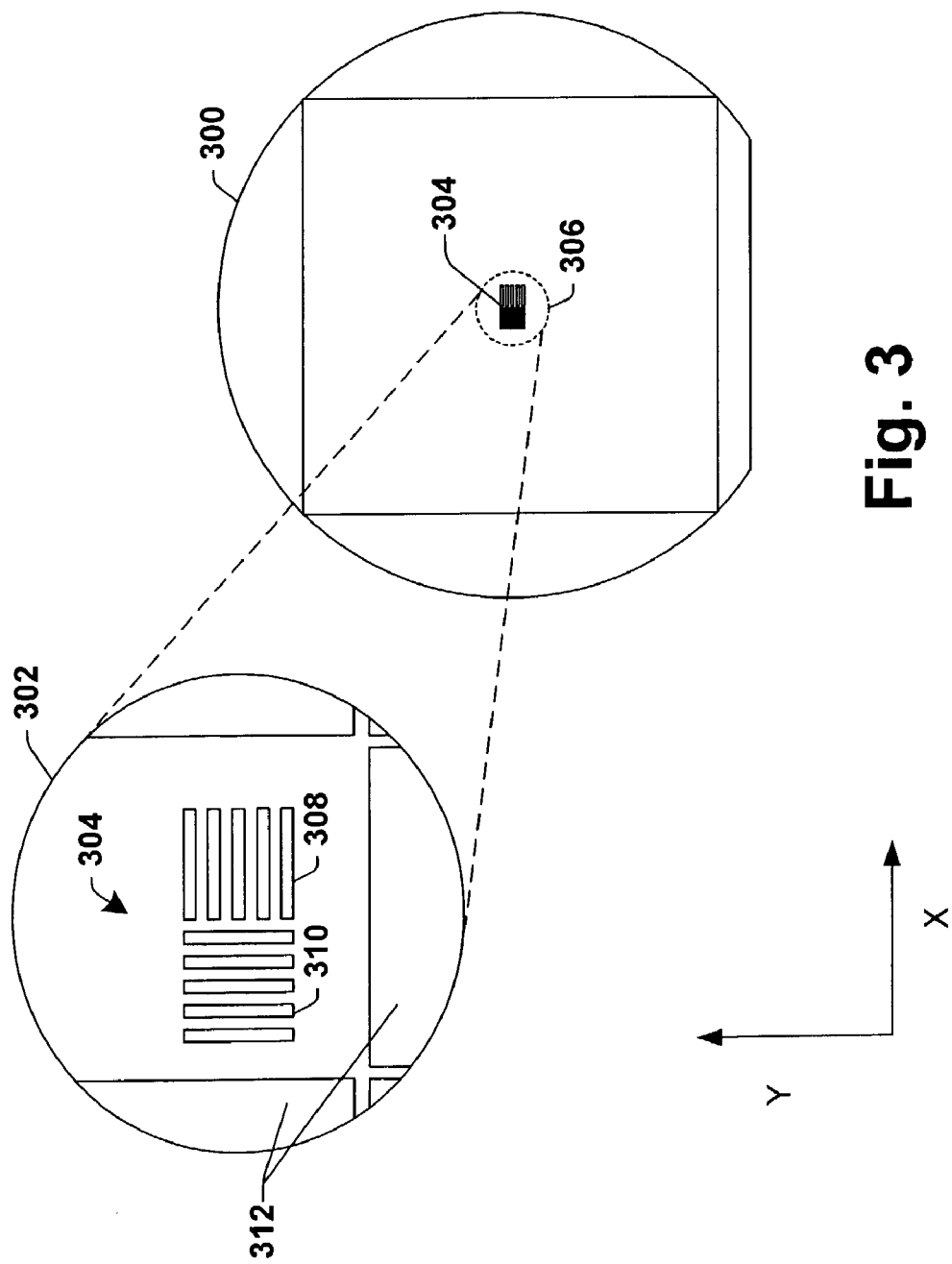
FIG. 3 is a top view of a structure, such as that depicted in FIG. 2, that can be utilized to concurrently measure critical dimensions and overlay with scatterometry.

FIG. 3 illustrates a top view of a substrate 300 (e.g., a wafer) and an enlargement 302 of overlying gratings 304 formed on a portion 306 (e.g., a die) of the wafer in accordance with one or more aspects of the present invention. The gratings can, for example, correspond to the overlying gratings depicted in FIG. 2 which, along with the underlying gratings shown in FIG. 2, facilitate concurrent measurement of critical dimensions and overlay with a scatterometry system. It is to be appreciated that no underlying gratings are depicted in FIG. 3 for purposes of simplicity. In the example shown, the overlying gratings 304 are formed both horizontally 308 and vertically 310 on the wafer. The vertical gratings 310 facilitate measuring overlay in an X-direction while the horizontal gratings 308 facilitate measuring overlay in a Y-direction with a single scatterometry system. It will be appreciated that such gratings can be oriented in any suitable direction(s) to obtain desired measurements. Also, the gratings can be located between production regions 312 of the substrate so as to maximize real estate associated with the device being manufactured. The particular gratings depicted in FIG. 3 include a series of elongated marks, which can be implemented as raised portions in the substrate or as troughs, such as etched into the substrate. It is to be appreciated that more complex (e.g., nonlinear) grating patterns and/or substrate features (e.g., lines, connectors, etc) could also be utilized in accordance with one or more aspects of the present invention.

Figure 4:
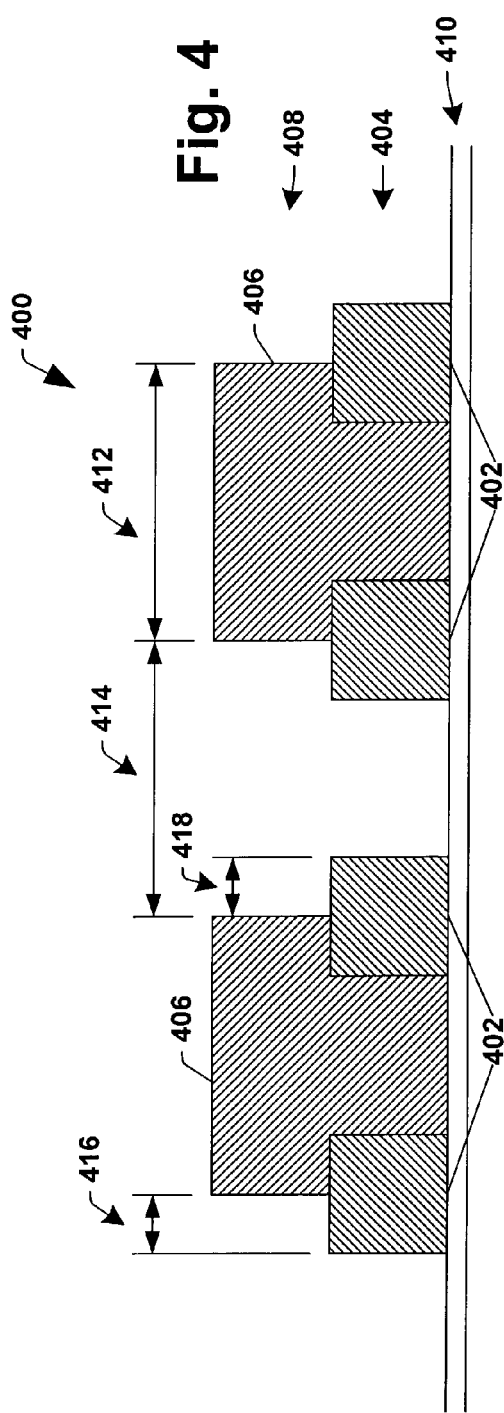
FIG. 4 is a cross sectional side view of a structure in accordance with one or more aspects of the present invention that facilitates concurrent measurement of critical dimensions and overlay with a scanning electron microscope (SEM).

FIG. 4 illustrates a cross sectional side view of a structure 400 according to one or more aspects of the present invention that facilitates concurrent measurement of critical dimensions and overlay with a scanning electron microscope (SEM). The structure can be formed on a portion (e.g., a die) of a wafer undergoing an IC fabrication process. By way of example and not limitation, one specific application for such a structure can be in an implant layer of a flash memory product. One or more gratings 402 are formed in a polysilicon layer 404 of the structure while one or more features 406 are formed within a resist layer 408 of the structure. Both the resist 408 and polysilicon 404 layers are formed over other underlying layers 410. The structure 400, and more particularly the features 406 in the resist layer 408, can be interrogated by an SEM system to reveal critical dimensions, such as line widths 412 and spacings 414 there-between. Similarly, overlay can be ascertained by finding the difference between first 416 and second 418 SEM interrogated measurements of underlying gratings 402. It will be appreciated that such a differencing function can be implemented by a simple software component. It will be further appreciated that the structure 400 can be formed at any suitable location on a wafer to obtain desired measurements.

Figure 5:
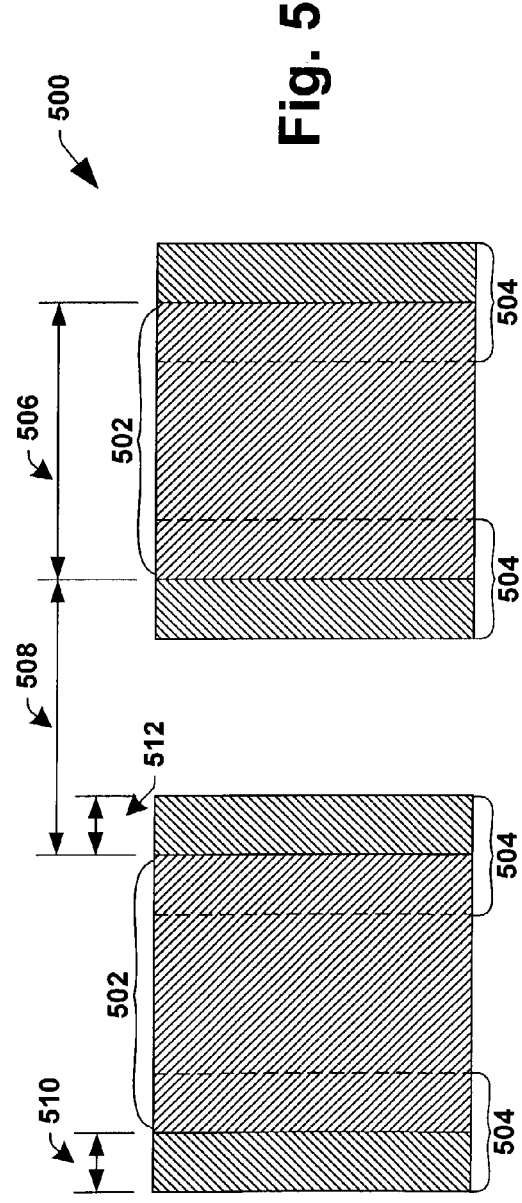
FIG. 5 is a top view of a structure, such as that depicted in FIG. 4, that can be utilized to concurrently measure critical dimensions and overlay with SEM.

FIG. 5 depicts a top view of a structure 500, such as that illustrated in FIG. 4. The structure 500 can be formed within a portion (e.g., a die) of a wafer and can be utilized for example, to concurrently measure critical dimensions and overlay in an implant layer in a flash memory product. The structure includes features 502 formed in a resist layer and gratings 504 formed under the resist layer in a polysilicon layer. Other layers (not shown) underlie both the resist and polysilicon layers. An SEM system can interrogate the features 502 in the resist layer to ascertain critical dimensions, such as line widths 506 and spaces 508 there-between. Overlay (and/or overlay error) can be determined by differencing SEM measurements of first 510 and second 512 grating portions that project out from under features formed in the resist layer.

Figure 6:
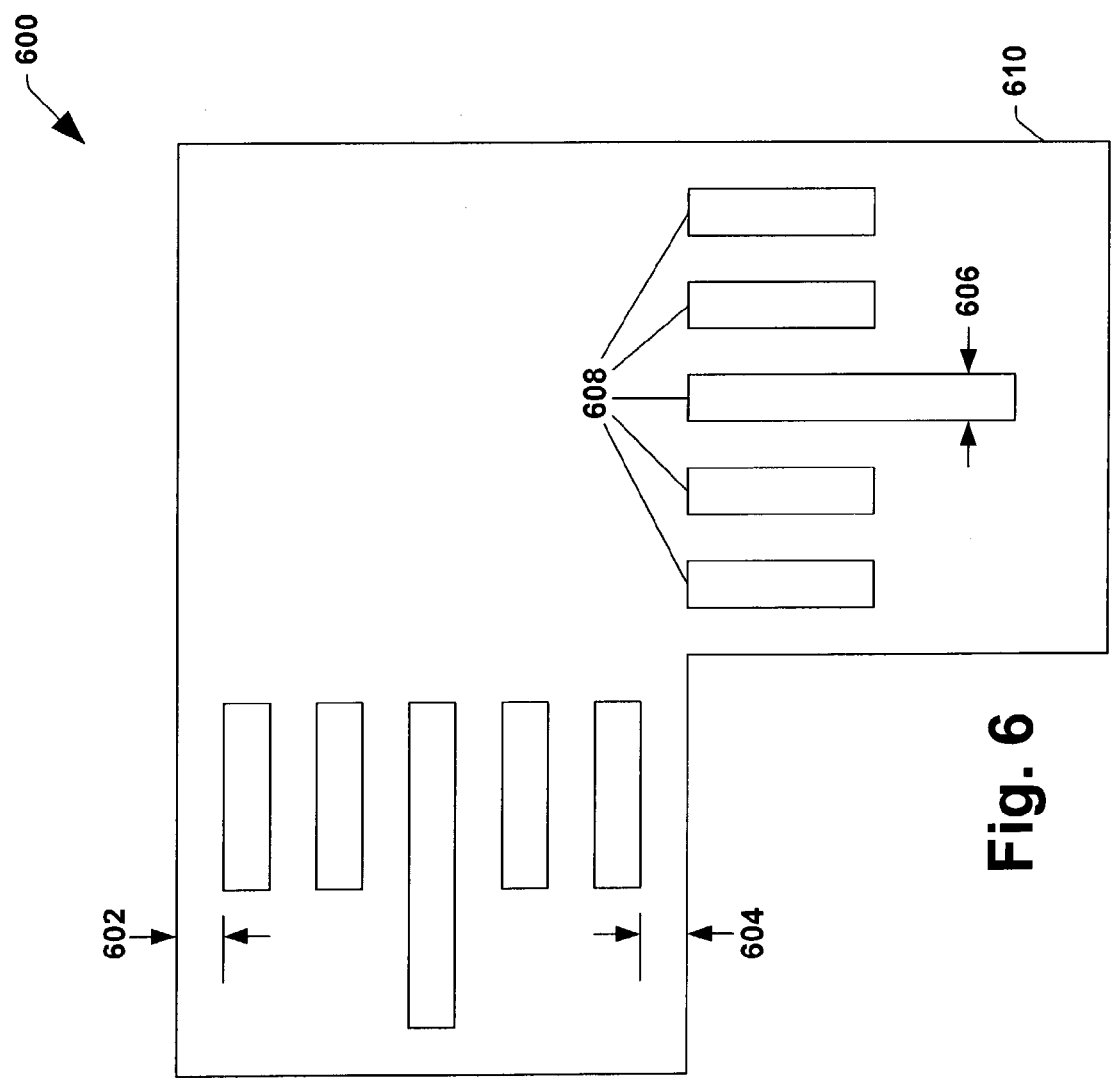
FIG. 6 is a cross sectional side view of an alternative structure that facilitates concurrent measurement of critical dimensions and overlay with SEM.

FIG. 6 illustrates an alternative structure 600 for concurrently measuring critical dimensions and overlay with an SEM system in accordance with one or more aspects of the present invention. The structure can be formed on a portion (e.g., a die) of a wafer undergoing an IC fabrication process. Overlay, including overlay error, can be determined by interrogating features on the wafer with an SEM system and finding differences in spacings between the features. For instance, respective values of two different spacing measurements 602, 604 can periodically be obtained and subtracted from one another throughout the fabrication process to determine if an overlay error is occurring. Critical dimensions 606 can be monitoring with an SEM system by interrogating gratings/features 608 printed within top or upper layers 610 of the wafer.

Figure 7:
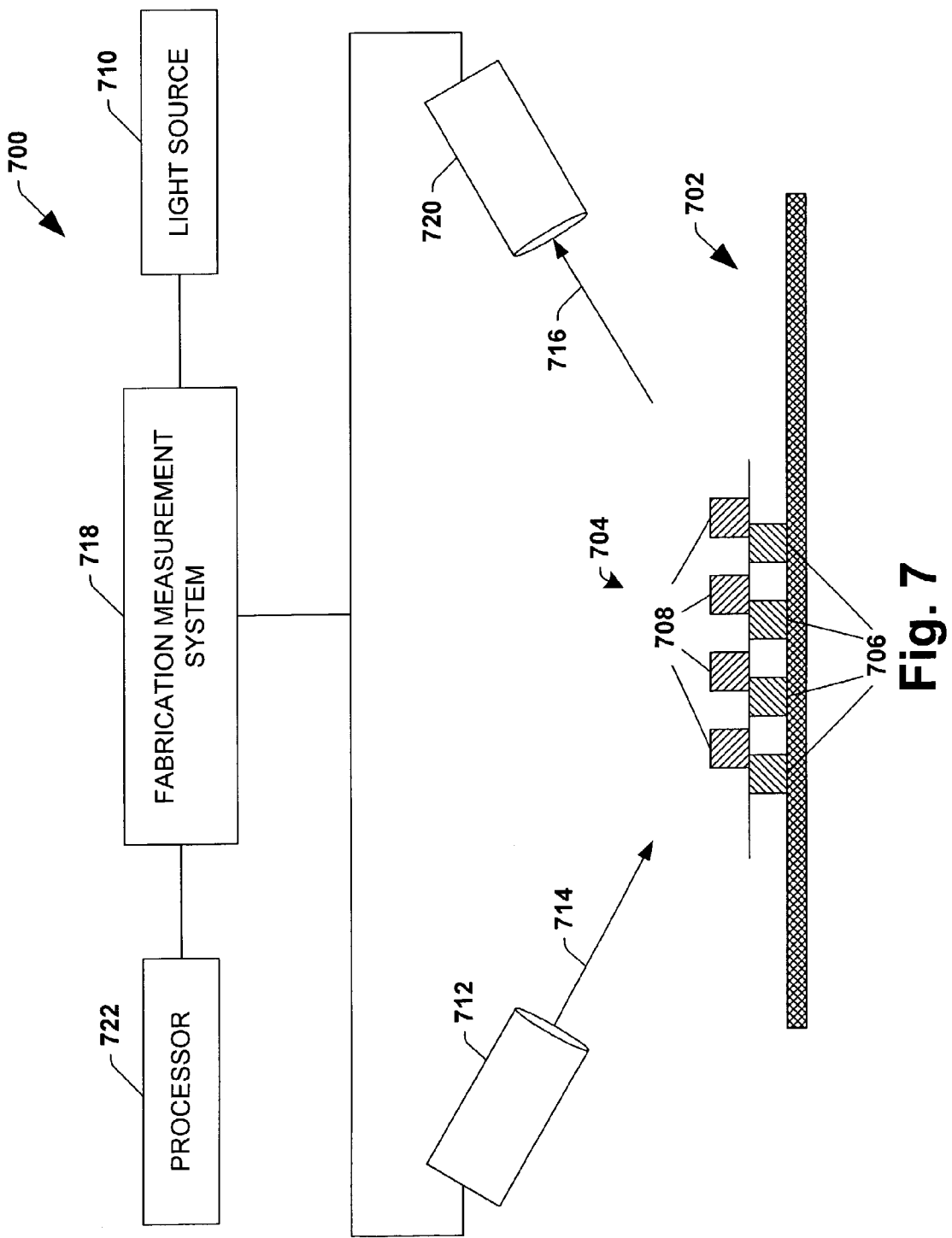
FIG. 7 illustrates a portion of a system for monitoring a semiconductor fabrication process with scatterometry according to one or more aspects of the present invention.

FIG. 7 illustrates a portion of a system 700 being employed to monitor (e.g., via scatterometry) a wafer 702 matriculating through a semiconductor fabrication process according to one or more aspects of the present invention. It will be appreciated that only a small portion of the wafer 702 is depicted in FIG. 7 for purposes of simplicity. The wafer 702 has a structure 704 formed thereon according to one or more aspects of the present invention. The structure includes one or more underlying gratings 706 that facilitate overlay measurements and alignment with other layers and one or more overlying gratings 708 that facilitate critical dimension measurements. The structure allows these measurements to be taken concurrently with a single measuring tool, thus mitigating fabrication equipment, time and spacing requirements while improving feature accuracy and chip quality control.

A light source 710 provides light to one or more light emitters 712 that direct a light 714 incident to the upper 708 and lower 706 gratings. The light 714 is reflected from the gratings as reflected light 716. The incident light 714 may be referred to as the reference beam, and thus the phase, intensity and/or polarization of the reference beam 714 may be recorded in a measurement system 718 to facilitate later comparisons to the reflected beam 716 (e.g., via signature comparison). The angle of the reflected light 716 from the gratings 706, 708 will vary in accordance with the evolving dimensions of the gratings and/or with the evolving dimensions of one or more patterns being developed in the wafer 702. Similarly, the intensity, phase and polarization properties of the specularly reflected light 716 may vary in accordance with the evolving dimensions. One or more light detecting components 720 collect the reflected light 716 and transmit the collected light, and/or data associated with the collected light, to the measurement system 718. The measurement system forwards this information to a processor 722, which may or may not be integral with the measurement system 718. The processor 722, or central processing unit (CPU), is programmed to control and carry out the various functions described herein. The processor 722 may be any of a plurality of processors, and the manner in which the processor can be programmed to carry out the functions described herein will be readily apparent to those having ordinary skill in the art based on the description provided herein. The reflected light 716 can, for example, be analyzed to generate one or more signatures that can be compared to one or more stored signatures to determine whether, for example, desired critical dimensions are being achieved and/or whether overlay error is occurring and thus whether, for example, feed forward and/or backward information should be generated and applied to selectively control and adjust one or more operating parameters of one or more IC fabrication components (e.g., alignment, post exposure baking, development, photolithography, etching, polishing, deposition) to achieve a desired result.

Figure 8:
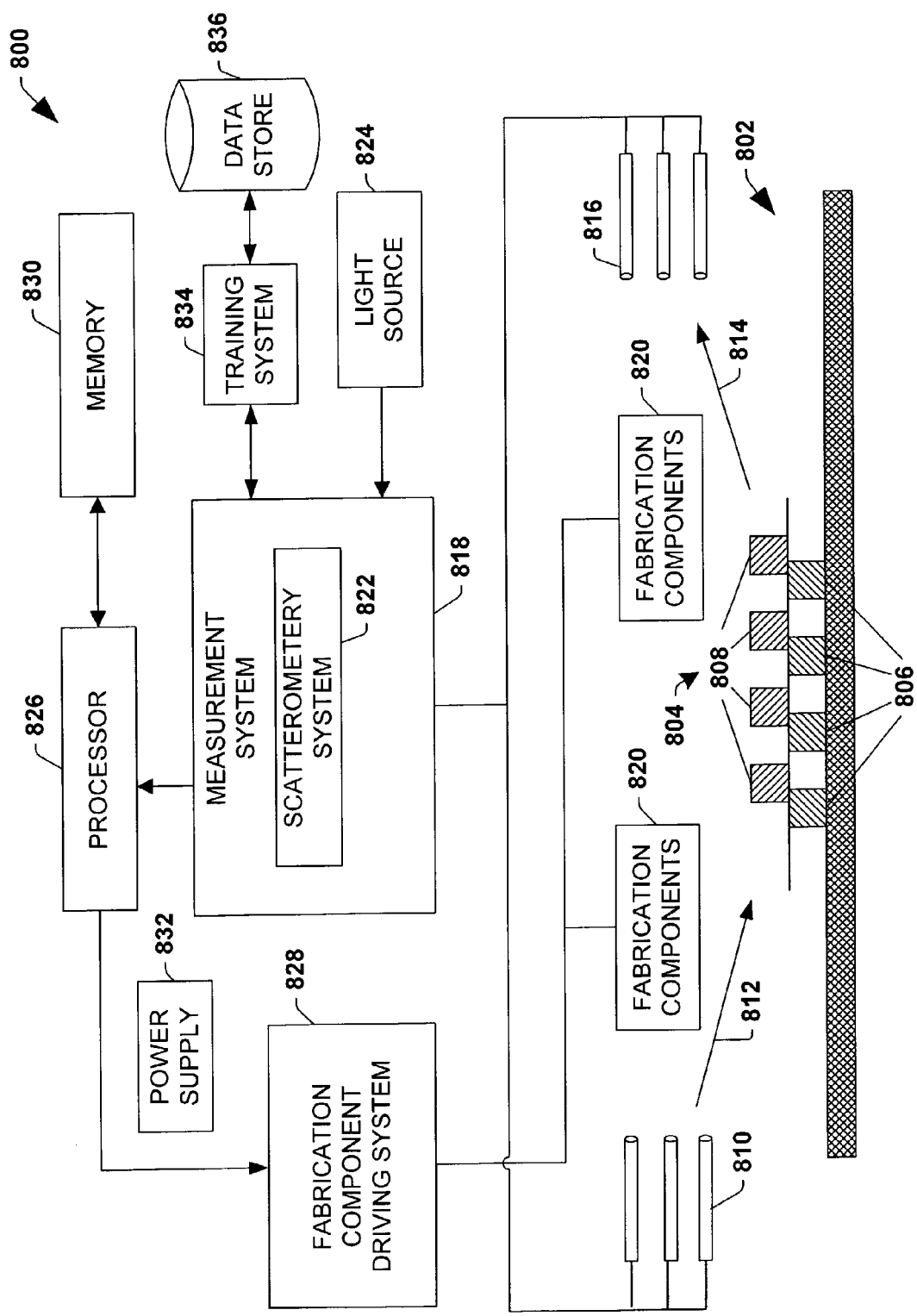
FIG. 8 illustrates a system for monitoring and controlling a semiconductor fabrication process according to one or more aspects of the present invention.

Turning to FIG. 8, a system 800 for monitoring and controlling a semiconductor fabrication process according to one or more aspects of the present invention is illustrated. A wafer 802, or a portion thereof, is depicted as undergoing the fabrication process and has a structure 804 formed thereon according to one or more aspects of the present invention. The structure facilitates concurrent measurement with scatterometry techniques of overlay and critical dimensions via one or more underlying gratings 806 and one or more overlying gratings 808, respectively.

One or more light sources 810 project light 812 onto respective portions of the structure 804, which cause the light to be reflected in different, quantifiable manners. Reflected light 814 is collected by one or more light detecting components 816, and processed by a measurement system 818 for a concurrent determination of critical dimensions and overlay. The reflected light 814 may, for example, be processed to generate signatures, which can be utilized to facilitate feedback and/or feed-forward control of one or more fabrication components 820 and/or operating parameters associated therewith as described herein to achieve desired critical dimensions and to mitigate overlay error.

The measurement system 818 includes a scatterometry system 822, which can be any scatterometry system suitable for carrying out aspects of the present invention as described herein. A source of light 824 (e.g., a laser, broadband radiation in the visible and near ultraviolet range, arc lamp, or a similar device) provides light to the one or more light sources 810 via the measurement system 818. Preferably, the light source 824 is a frequency stabilized laser, however, it will be appreciated that any laser (e.g., laser diode or helium neon (HeNe) gas laser) or other light source suitable for carrying out the present invention may be employed. Similarly, any one or more light detecting components 816 suitable for carrying out aspects of the present invention may be employed (e.g., photo detector, photo diodes) for collecting reflected light.

A processor 826 receives the measured data from the measurement system 818 and is programmed to control and operate the various components within the system 800 in order to carry out the various functions described herein. The processor, or CPU 826, may be any of a plurality of processors, and the manner in which the processor 826 can be programmed to carry out the functions described herein will be readily apparent to those having ordinary skill in the art based on the description provided herein.

The processor 826 is also coupled to a fabrication component driving system 828 that drives the fabrication components 820. The processor 826 controls the fabrication component driving system 828 to selectively control one or more of the fabrication components 820 and/or one or more operating parameters associated therewith as described herein. The processor 826 monitors the process via the signatures generated by the reflected and/or diffracted light, and selectively regulates the fabrication process by controlling the corresponding fabrication components 820. Such regulation enables controlling critical dimensions and overlay error during fabrication and further facilitates initiating a subsequent fabrication phase with more precise initial data, which facilitates improved chip quality at higher packing densities.

Though not shown in FIG. 8, it should be appreciated that the fabrication components 820 may be separate and independent from the measurement system 818 (e.g., SEM, scatterometry system 822). For example, the measurement system 818 may be linked and/or networked to the fabrication components 820 (e.g., an etcher tool) via a computer network (not shown). Measurements taken from the measurement system 818 may be communicated via the network to the etcher tool in order to adjust times, concentrations, and the like. Moreover, the fabrication components 820 and the measurement system 818 may be in the system 800 but either integrated on the same tool or as separate tools, depending on the application and as desired by a user.

A memory 830 is also shown in the example illustrated in FIG. 8. The memory 830 is operable to store, among other things, program code executed by the processor 826 for carrying out one or more of the functions described herein. The memory may include, for example, read only memory (ROM) and random access memory (RAM). The RAM is the main memory into which the operating system and application programs are loaded. The memory 830 may also serve as a storage medium for temporarily storing information and data that may be useful in carrying out one or more aspects of the present invention. For mass data storage, the memory 830 may also include a hard disk drive (e.g., 50 Gigabyte hard drive).

A power supply 832 is included to provide operating power to one or more components of the system 800. Any suitable power supply 832 (e.g., battery, line power) can be employed to carry out the present invention.

A training system 834 may also be included. The training system 834 may be adapted to populate a data store 836 (which may be comprised within the memory 830) for use in subsequent monitoring. For example, the scatterometry system 822 can generate substantially unique scatterometry signatures that can be stored in the data store 836 via the training system 834. The data store 836 can be populated with an abundance of scatterometry signatures by examining a series of wafers and/or wafer dies. Scatterometry signatures can be compared to scatterometry measurements stored in the data store 836 to generate feed forward/backward control data that can be employed to control the fabrication process. It is to be appreciated that the data store 836 can store data in data structures including, but not limited to one or more lists, arrays, tables, databases, stacks, heaps, linked lists and data cubes. Furthermore the data store 836 can reside on one physical device and/or may be distributed between two or more physical devices (e.g., disk drives, tape drives, memory units).

Figure 9:
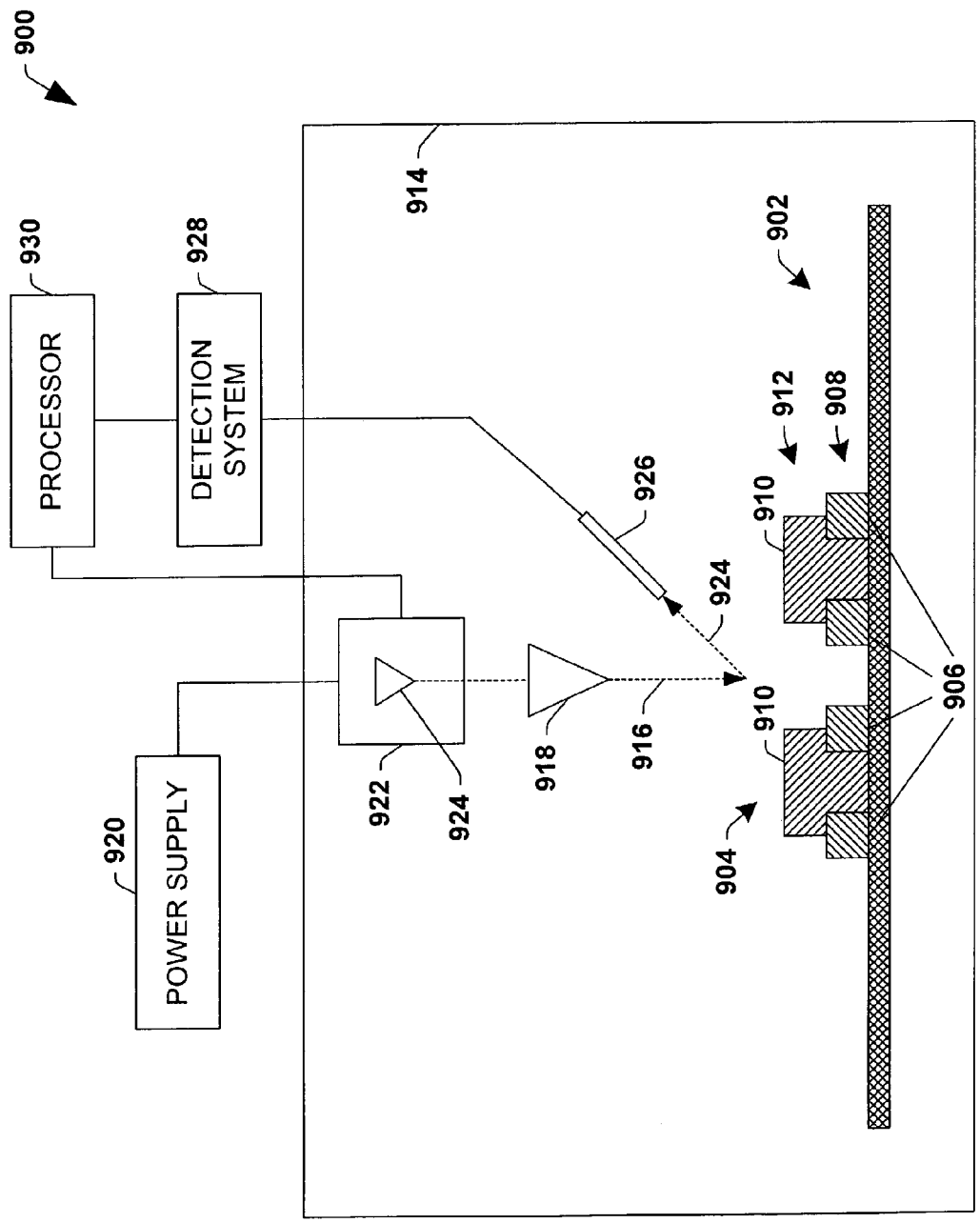
FIG. 9 illustrates a portion of a system for monitoring a semiconductor fabrication process with SEM according to one or more aspects of the present invention.

FIG. 9 illustrates a portion of a system 900 being employed to monitor (e.g., via SEM) the development of a wafer 902 undergoing a semiconductor fabrication process. It will be appreciated that only a small portion of the wafer is depicted in FIG. 9 for purposes of simplicity. The wafer 902 has a structure 904 formed thereon according to one or more aspects of the present invention. By way of example and not limitation, one specific application for such a structure can be in an implant layer of a flash memory product. One or more gratings 906 are formed in a polysilicon layer 908 of the structure while one or more features 910 are formed within a resist layer 912 of the structure 904. The structure 904, and more particularly the features 910 in the resist layer 912, can be interrogated by an SEM system to reveal critical dimensions, such as line widths and spacings there-between. Similarly, overlay and overlay error, in particular, can be ascertained by finding the difference between first and second SEM interrogated measurements of underlying gratings that jut out from under the features. The structure 904 allows these measurements to be taken concurrently with a single measuring tool, thus mitigating fabrication equipment, time and spacing requirements while improving precision and quality control.

The wafer 902 is housed within a chamber 914 and is interrogated by an electron beam 916 protected from an electromagnetic lens 918. The electron beam 916 is created from high voltage supplied by a power supply 920 associated with a beam generating system 922 which includes an emission element 924. Various directing, focusing, and scanning elements (not shown) in the beam generating system 922 guide the electron beam 916 from the emission element (924) to the electromagnetic lens 918. The electron beam particles can be accelerated to energies from about 500 eV to 40 Kev which can yield, for example, resolutions from about 30 to about 40 Angstroms. When the electron beam 916 strikes a surface, electrons and x-rays, for example, are emitted 924, are detected by a detector 926, and are provided to a detection system 928. The most useful electron signals 924 are low energy secondary electrons that provide a substantial amount of current to the detector 926. Examples of electron signals 924 include backscattered electrons, reflected electrons, secondary electrons, x-rays, current, and the like.

The detection system 928 can digitize the signal from the detector 926 and/or provide filtering or other signal processing to the information. The detection system 928 forwards this information to a processor 930, which may or may not be integral with the detection system 928. The processor 930, or central processing unit (CPU), is programmed to control and carry out the various functions described herein. The processor 930 may be any of a plurality of processors, and the manner in which the processor 930 can be programmed to carry out the functions described herein will be readily apparent to those having ordinary skill in the art based on the description provided herein.

For example, the processor 930 may control the beam generating system 922 and perform signal analysis. The electron signals 924 can be analyzed to generate one or more signatures that can be compared to one or more stored signatures to determine whether, for example, desired critical dimensions are being achieved and/or whether overlay error is occurring and thus whether, for example, feed forward and/or backward information should be generated and applied to selectively control and adjust one or more operating parameters of one or more IC fabrication components (e.g., alignment, post exposure baking, development, photolithography, etching, polishing, deposition) to achieve a desired result.

Alternatively or in addition, the electron signals 924 may be analyzed directly by an algorithm in order to obtain a measurement. Thus, generating a signature may be optional depending on the application and as desired by a user. Likewise, comparing a generated signature to a signature database and/or maintaining a signature database may also be optional according to the user's preferences.

It will be appreciated that relative movement between the beam 916 and the wafer 902 can be controlled to facilitate obtaining desired measurements. The electron beam 916 can, for example, scan from point to point in a rectangular raster pattern to facilitate measurement of the width of a conductor, for example. Accelerating voltage, beam current and spot diameter can also be controlled to achieve desired measurements.

Figure 10:
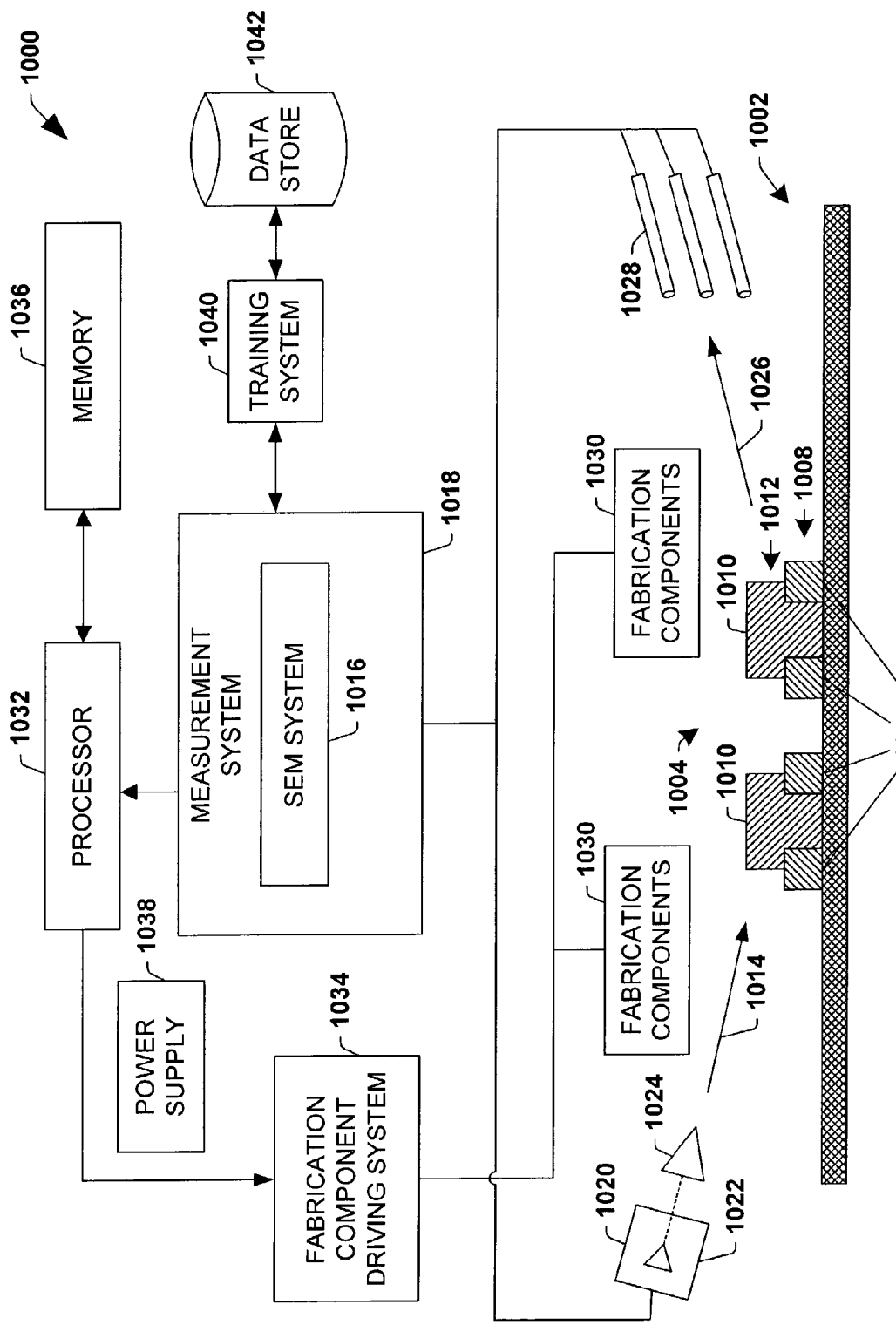
FIG. 10 illustrates another system for monitoring and controlling a semiconductor fabrication process according to one or more aspects of the present invention.

Turning to FIG. 10, a system 1000 for monitoring and controlling a semiconductor fabrication process according to one or more aspects of the present invention is illustrated. A wafer 1002 or a portion thereof depicted as undergoing the fabrication process has a structure 1004 formed thereon according to one or more aspects of the present invention. The structure 1004 facilitates concurrent measurement of overlay and critical dimensions with SEM techniques. The structure can, for example, be in an implant layer of a flash memory product. One or more gratings 1006 are formed in a polysilicon layer 1008 of the structure 1004 while one or more features 1010 are formed within a resist layer 1012 of the structure 1004. The structure 1004, and more particularly the features 1010 in the resist layer 1012, can be interrogated by an SEM system to reveal critical dimensions, such as line widths and spacings there-between. Similarly, overlay and/or overlay error can be ascertained by finding the difference between first and second SEM interrogated measurements of underlying gratings that extend out from under the features 1010.

The wafer 1002 is interrogated by an electron beam 1014 projected onto respective portions of the structure. The electron beam 1014 is part of an SEM system 1016, at least part of which may be integral with a measurement system

1018. The electron beam 1014 is created from high voltage in a beam generating system 1020 of the SEM which includes an emission element 1022. Various directing, focusing, and scanning elements (not shown) in the beam generating system 1020 guide the electron beam 1014 from the emission element 1022 to an electromagnetic lens 1024. When the electron beam 1014 strikes the structure 1004, electrons and x-rays, for example, are emitted 1026 and are detected by one or more detectors 1028 and are provided to the measurement system 1018 for a concurrent determination of critical dimensions and overlay. The detected electrons may be processed to generate signatures, which can be utilized to facilitate feedback and/or feed-forward control of one or more fabrication components 1030 and/or operating parameters associated therewith as described herein to achieve desired critical dimensions and to mitigate overlay error.

Alternatively, the detected electrons may be automatically and directly analyzed by any number of algorithms to yield measurements without comparison or reference to stored signatures. Thus, processing time may be increased as well as the overall efficiency of the system 1000.

A processor 1032 receives the measured data from the measurement system 1018 and is programmed to control and operate the various components within the system 1000 in order to carry out the various functions described herein. The processor, or CPU 1032, may be any of a plurality of processors, and the manner in which the processor 1032 can be programmed to carry out the functions described herein will be readily apparent to those having ordinary skill in the art based on the description provided herein.

The processor 1032 is also coupled to a fabrication component driving system 1034 that drives the fabrication components 1030. The processor 1032 controls the fabrication component driving system 1034 to selectively control one or more of the fabrication components 1030 and/or one or more operating parameters associated therewith as described herein. The processor 1032 monitors the process via the optional signatures generated by the detected electrons, and selectively regulates the fabrication process by controlling the corresponding fabrication components 1030. Such regulation enables controlling critical dimensions and overlay (e.g., overlay error) during fabrication and further facilitates initiating a subsequent fabrication phase with more precise initial data, which facilitates improved chip quality at higher packing densities.

A memory 1036 is also shown in the example illustrated in FIG. 10. The memory 1036 is operable to store, among other things, program code executed by the processor 1032 for carrying out one or more of the functions described herein. The memory 1036 may include, for example, read only memory (ROM) and random access memory (RAM). The RAM is the main memory into which the operating system and application programs are loaded. The memory 1036 may also serve as a storage medium for temporarily storing information and data that may be useful in carrying out one or more aspects of the present invention. For mass data storage, the memory 1036 may also include a hard disk drive (e.g., 50 Gigabyte hard drive).

A power supply 1038 is included to provide operating power to one or more components of the system 1000. Any suitable power supply 1038 (e.g., battery, line power) can be employed to carry out the present invention.

A training system 1040 may also be included. The training system 1040 may be adapted to populate a data store 1042 (which may be comprised within the memory 1036 for use in subsequent monitoring. For example, the SEM system 1016 can generate substantially unique signatures that can be stored in the data store 1042 via the training system 1040. The data store 1042 can be populated with an abundance of SEM signatures by examining a series of wafers and/or wafer dies. SEM signatures can be compared to SEM measurements stored in the data store 1042 to generate feed forward/backward control data that can be employed to control the fabrication process. It is to be appreciated that the data store 1042 can store data in data structures including, but not limited to one or more lists, arrays, tables, databases, stacks, heaps, linked lists and data cubes. Furthermore, the data store 1042 can reside on one physical device and/or may be distributed between two or more physical devices (e.g., disk drives, tape drives, memory units).

Figures 11, 12, 13:
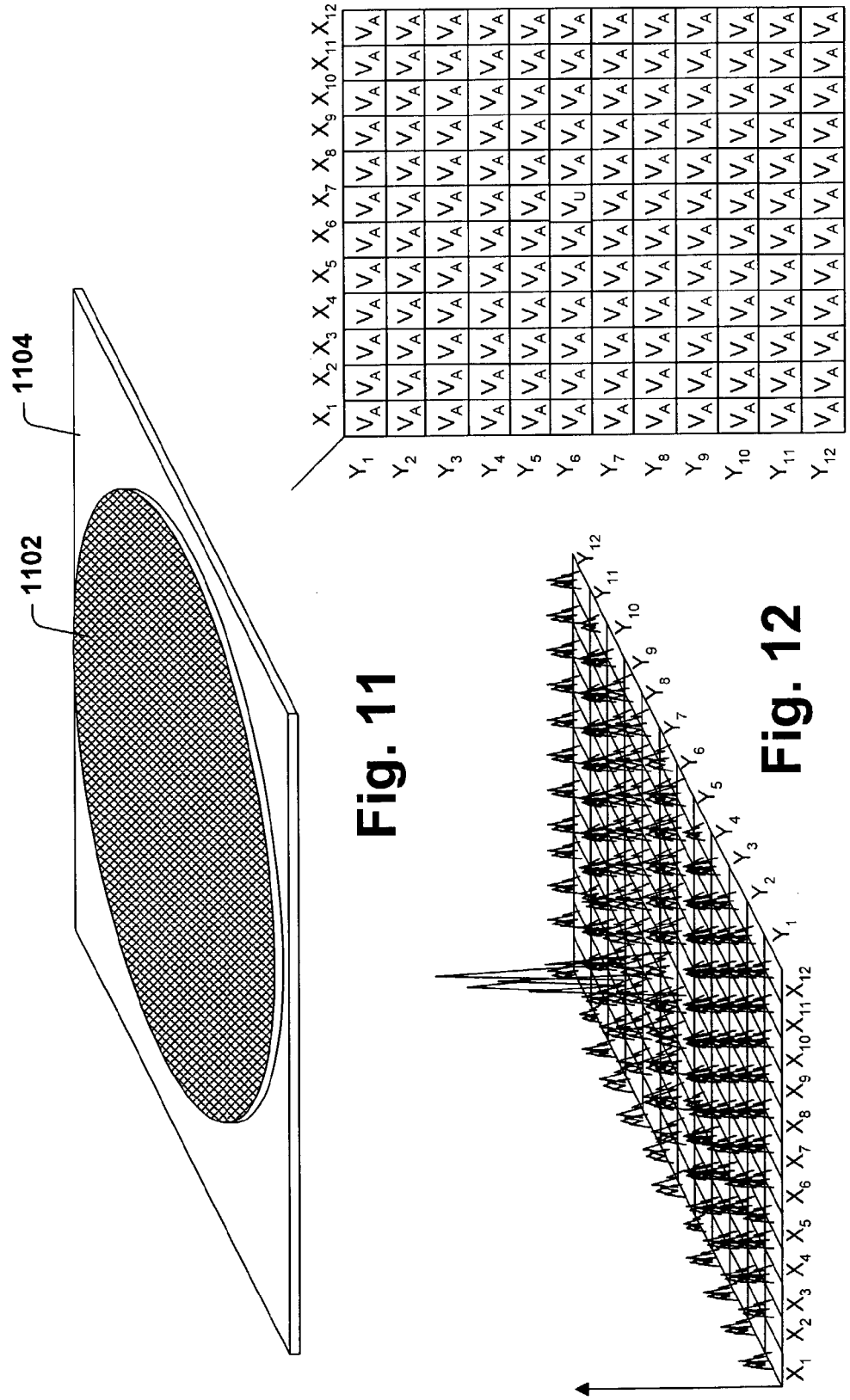
FIG. 11 illustrates a perspective view of a grid mapped wafer according to one or more aspects of the present invention.
FIG. 12 illustrates plots of measurements taken at grid mapped locations on a wafer in accordance with one or more aspects of the present invention.
FIG. 13 illustrates a table containing entries corresponding to measurements taken at respective at grid mapped locations on a wafer in accordance with one or more aspects of the present invention.

Turning now to FIGS. 11–13, in accordance with one or more aspects of the present invention, a wafer 1102 (or one or more die located thereon) situated on a stage 1104 may be logically partitioned into grid blocks to facilitate concurrent measurements of critical dimensions and overlay as the wafer matriculates through a semiconductor fabrication process. This may facilitate selectively determining to what extent, if any, fabrication adjustments are necessary. Obtaining such information may also assist in determining problem areas associated with fabrication processes.

FIG. 11 illustrates a perspective view of a steppable stage 1104 supporting a wafer 1102. The wafer 102 may be divided into a grid pattern as shown in FIG. 12.

Each grid block (XY) of the grid pattern corresponds to a particular portion of the wafer 1102 (e.g., a die or a portion of a die). The grid blocks are individually monitored for fabrication progress by concurrently measuring critical dimensions and overlay with either scatterometry or scanning electron microscope (SEM) techniques.

This may also be applicable in order to assess wafer-to-wafer and lot-to-lot variations. For example, a portion P (not shown) of a first wafer (not shown) may be compared to the corresponding portion P (not shown) of a second wafer. Thus, deviations between wafers and lots may be determined in order to calculate adjustments to the fabrication components which are necessary to accommodate for the wafer-to-wafer and/or lot-to-lot variations.

In FIG. 12, one or more respective portions of a wafer 1102 ($X_1Y_1 \ldots X_{12}, Y_{12}$) are concurrently monitored for critical dimensions and overlay utilizing either scatterometry or scanning electron microscope techniques. Exemplary measurements produced during fabrication for each grid block are illustrated as respective plots. The plots can, for example, be composite valuations of signatures of critical dimensions and overlay. Alternatively, critical dimensions and overlay values may be compared separately to their respective tolerance limits.

As can be seen, the measurement at coordinate $X_7Y_6$ yields a plot that is substantially higher than the measurement of the other portions XY. This can be indicative of overlay, overlay error, and/or one or more critical dimension outside of acceptable tolerances. As such, fabrication components and/or operating parameters associated therewith can be adjusted accordingly to mitigate repetition of this aberrational measurement. It is to be appreciated that the wafer 1102 and or one or more die located thereon may be mapped into any suitable number and/or arrangement of grid blocks to effect desired monitoring and control.

FIG. 13 is a representative table of concurrently measured critical dimensions and overlay taken at various portions of the wafer 1102 mapped to respective grid blocks. The measurements in the table can, for example, be amalgams of respective critical dimension and overlay signatures. As can be seen, all the grid blocks, except grid block $X_7Y_6$, have measurement values corresponding to an acceptable value ($V_A$) (e.g., no overlay error is indicated and/or overlay measurements and critical dimensions are within acceptable tolerances), while grid block $X_7Y_6$ has an undesired value ($V_U$) (e.g., overlay and critical dimensions are not within acceptable tolerances, thus at least an overlay or CD error exists). Thus, it has been determined that an undesirable fabrication condition exists at the portion of the wafer 1102 mapped by grid block $X_7Y_6$. Accordingly, fabrication process components and parameters may be adjusted as described herein to adapt the fabrication process accordingly to mitigate the re-occurrence or exaggeration of this unacceptable condition.

Alternatively, a sufficient number of grid blocks may have desirable thickness measurements so that the single offensive grid block does not warrant scrapping the entire wafer. It is to be appreciated that fabrication process parameters may be adapted so as to maintain, increase, decrease and/or qualitatively change the fabrication of the respective portions of the wafer 1102 as desired. For example, when the fabrication process has reached a predetermined threshold level (e.g., X % of grid blocks have acceptable CDs and no overlay error exists), a fabrication step may be terminated.

Figure 14:
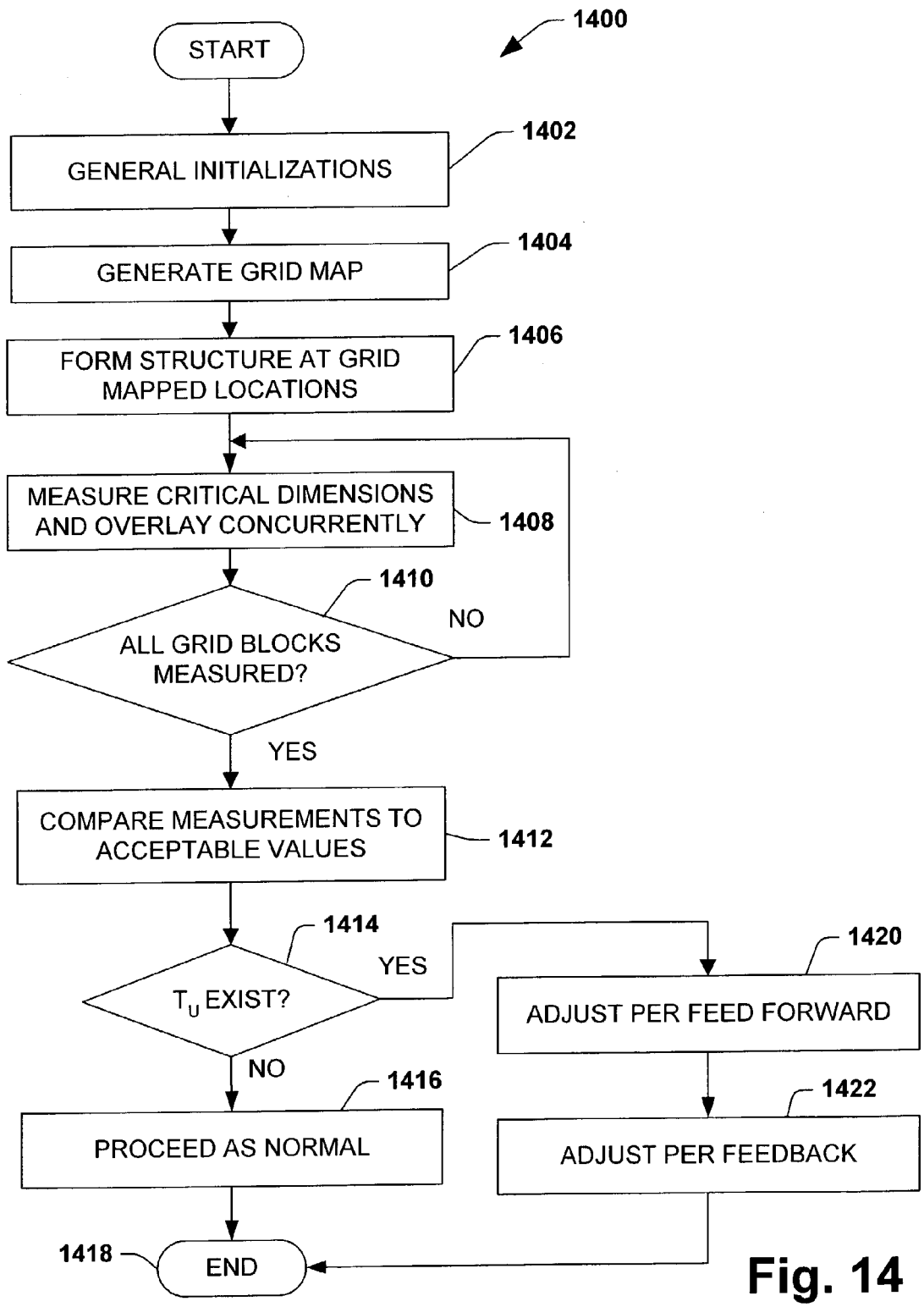
FIG. 14 is flow diagram illustrating a methodology for monitoring and controlling an IC fabrication process according to one or more aspects of the present invention.

In view of the exemplary systems shown and described above, a methodology, which may be implemented in accordance with one or more aspects of the present invention, will be better appreciated with reference to the flow diagram of FIG. 14. While, for purposes of simplicity of explanation, the methodology is shown and described as a series of function blocks, it is to be understood and appreciated that the present invention is not limited by the order of the blocks, as some blocks may, in accordance with the present invention, occur in different orders and/or concurrently with other blocks from that shown and described herein. Moreover, not all illustrated blocks may be required to implement a methodology in accordance with one or more aspects of the present invention. It is to be appreciated that the various blocks may be implemented via software, hardware a combination thereof or any other suitable means (e.g., device, system, process, component) for carrying out the functionality associated with the blocks. It is also to be appreciated that the blocks are merely to illustrate certain aspects of the present invention in a simplified form and that these aspects may be illustrated via a lesser and/or greater number of blocks.

FIG. 14 is flow diagram illustrating a methodology 1400 for monitoring and controlling an IC fabrication process according to one or more aspects of the present invention. The methodology begins at 1402 wherein general initializations are performed. Such initializations can include, but are not limited to, establishing pointers, allocating memory, setting variables, establishing communication channels and/or instantiating one or more objects. At 1404, a grid map comprising one or more grid blocks "XY" is generated. Such grid blocks may correspond to dies on the wafer and or to portions of one or more die on a wafer, for example.

At 1406, a structure such as that described herein is formed at respective grid mapped locations on the wafer to facilitate concurrent measurement of critical dimensions and overlay with either scatterometry or scanning electron microscope (SEM) techniques at the grid mapped locations. At 1408, as the wafer matriculates through the fabrication process, overlay and critical dimensions, such as depth, width, height, slope, and the like, are concurrently measured with either scatterometry or SEM at the grid mapped locations via the structure formed at the respective locations.

At 1410, a determination is made as to whether measurements have been taken at all (or a sufficient number) of grid mapped locations. If the determination at 1410 is NO, then processing returns to 1408 so that additional measurements can be made. If the determination at 1400 is YES, then at 1412 the measurements are compared to acceptable values to determine if an overlay error is occurring and/or if critical dimensions are within acceptable tolerances.

By way of example, measurements of critical dimensions and overlay can be analyzed to produce signatures. These signatures can then be compared to acceptable signature values for critical dimensions and overlay at the grid mapped locations. Additionally, respective critical dimension and overlay signatures can be aggregated for the respective grid mapped locations to produce a single value for comparison to an acceptable value for the grid mapped locations. At 1414, a determination is made as to whether an undesired value ($V_U$) has been encountered (e.g., indicating that an overlay error is occurring and/or that one or more critical dimensions are outside of acceptable tolerances).

If the determination at 1414 is NO, then at 1416 processing continues as normal. The methodology can then advance to 1418 and end. If, however, the determination at 1414 is YES, meaning that an undesired value was encountered, then at 1420, one or more fabrications components and/or operating parameters associated therewith can be adjusted as described herein according to feed forward control data derived from the measurements to mitigate or remedy the situation. For example, an exposing source can be turned off and/or data generated by sophisticated modeling techniques can be fed forward to post exposure baking and/or development stages to control processing parameters such as bake time and/or temperature to bring critical dimensions back to within acceptable tolerances and/or to mitigate overlay error.

At 1422, control data derived from the measurements can also be feed back to adjust one or more fabrications components and/or operating parameters associated therewith to mitigate reoccurrence of the undesired event during subsequent processing. For instance, stepped alignment of the wafer can be adjusted to facilitate proper placement of a line on subsequently processed dies. Similarly, exposure time and/or intensity can be controlled so that a line having a proper width is formed within a photoresist layer. The methodology then ends at 1418. As mentioned above, events can occur in orders different from that depicted in FIG. 14. For example, measurements taken, as at 1406, can be compared to acceptable values, as at 1412, prior to determining whether measurements have been taken at all grid mapped locations, as at 1410.

Figure 15:
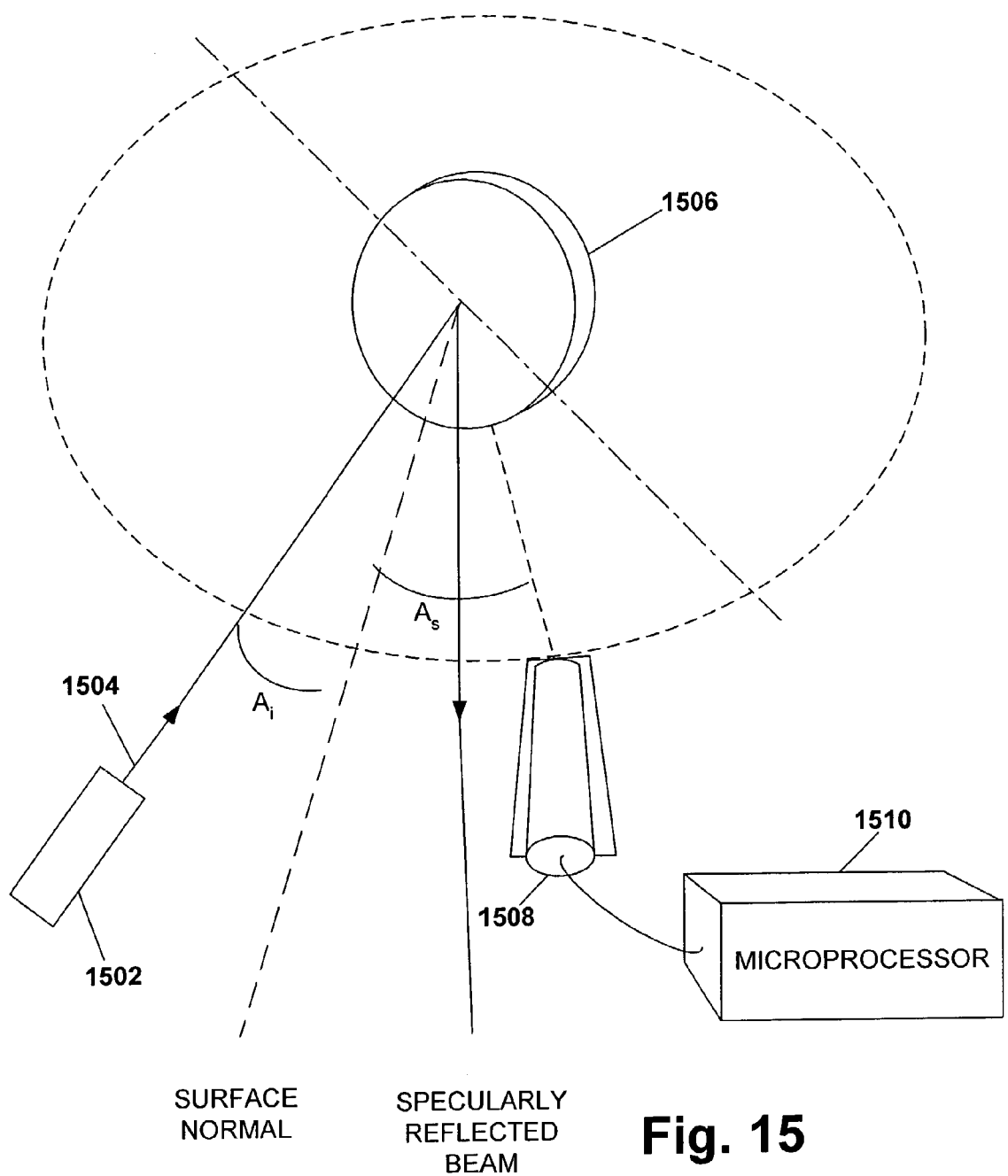
FIG. 15 illustrates an exemplary scatterometry system suitable for implementation with one or more aspects of the present invention.

FIG. 15 illustrates an exemplary scatterometry system suitable for implementation with one or more aspects of the present invention. Light from a laser 1502 is brought to focus in any suitable manner to form a beam 1504. A sample, such as a wafer 1506, is placed in the path of the beam 1504 and a photo detector or photo multiplier 1508 of any suitable construction. Different detector methods and arrangements may be employed to determine the scattered and/or reflected power. A microprocessor 1510, of any suitable design, may be used to process detector readouts, including, but not limited to, intensity properties of the specularly reflected light, polarization properties of the specularly reflected light, and angular locations of different diffracted orders. Thus, light reflected from the sample 1506 may be accurately measured.

Concepts of scatterometry and how they are employed in accordance with one or more aspects of the present invention are discussed with respect to FIGS. 16–21. Scatterometry is a technique for extracting information about a surface upon which an incident light has been directed. Scatterometry is a metrology that relates the geometry of a sample to its scattering effects. Scatterometry is based optical diffraction responses. Scatterometry can be employed to acquire information concerning properties including, but not limited to, horizontal/vertical alignment/shifting/compression/stretching, dishing, erosion, profile and critical dimensions of a surface and/or features present on a surface. The information can be extracted by comparing the phase and/or intensity of a reference light directed onto the surface with phase and/or intensity signals of a complex reflected and/or diffracted light resulting from the incident light reflecting from and/or diffracting through the surface upon which the incident light was directed. The intensity and/or the phase of the reflected and/or diffracted light will change based on properties of the surface upon which the light is directed. Such properties include, but are not limited to, the planarity of the surface, features on the surface, voids in the surface, the number and/or type of layers beneath the surface.

Different combinations of the above-mentioned properties will have different effects on the phase and/or intensity of the incident light resulting in substantially unique intensity/phase signatures in the complex reflected and/or diffracted light. Thus, by examining a signal (signature or stored value) library of intensity/phase signatures, a determination can be made concerning the properties of the surface. Such substantially unique intensity/phase signatures are produced by light reflected from and/or refracted by different surfaces due, at least in part, to the complex index of refraction of the surface onto which the light is directed. The complex index of refraction (N) can be computed by examining the index of refraction (n) of the surface and an extinction coefficient (k). One such computation of the complex index of refraction can be described by the equation:

$$N = n - jk, \text{ where } j \text{ is an imaginary number.}$$

The signal (signature) library can be constructed from observed intensity/phase signatures and/or signatures generated by modeling and simulation. By way of illustration, when exposed to a first incident light of known intensity, wavelength and phase, a wafer can generate a first intensity/phase signature. Observed signatures can be combined with simulated and modeled signatures to form a signal (signature) library. Simulation and modeling can be employed to produce signatures against which measured intensity/phase signatures can be matched. In one exemplary aspect of the present invention, simulation, modeling and observed signatures are stored in a signal (signature) data store. Thus, when intensity/phase signals are received from scatterometry detecting components, the intensity/phase signals can be pattern matched, for example, to the library of signals to determine whether the signals correspond to a stored signature.

Figure 16:
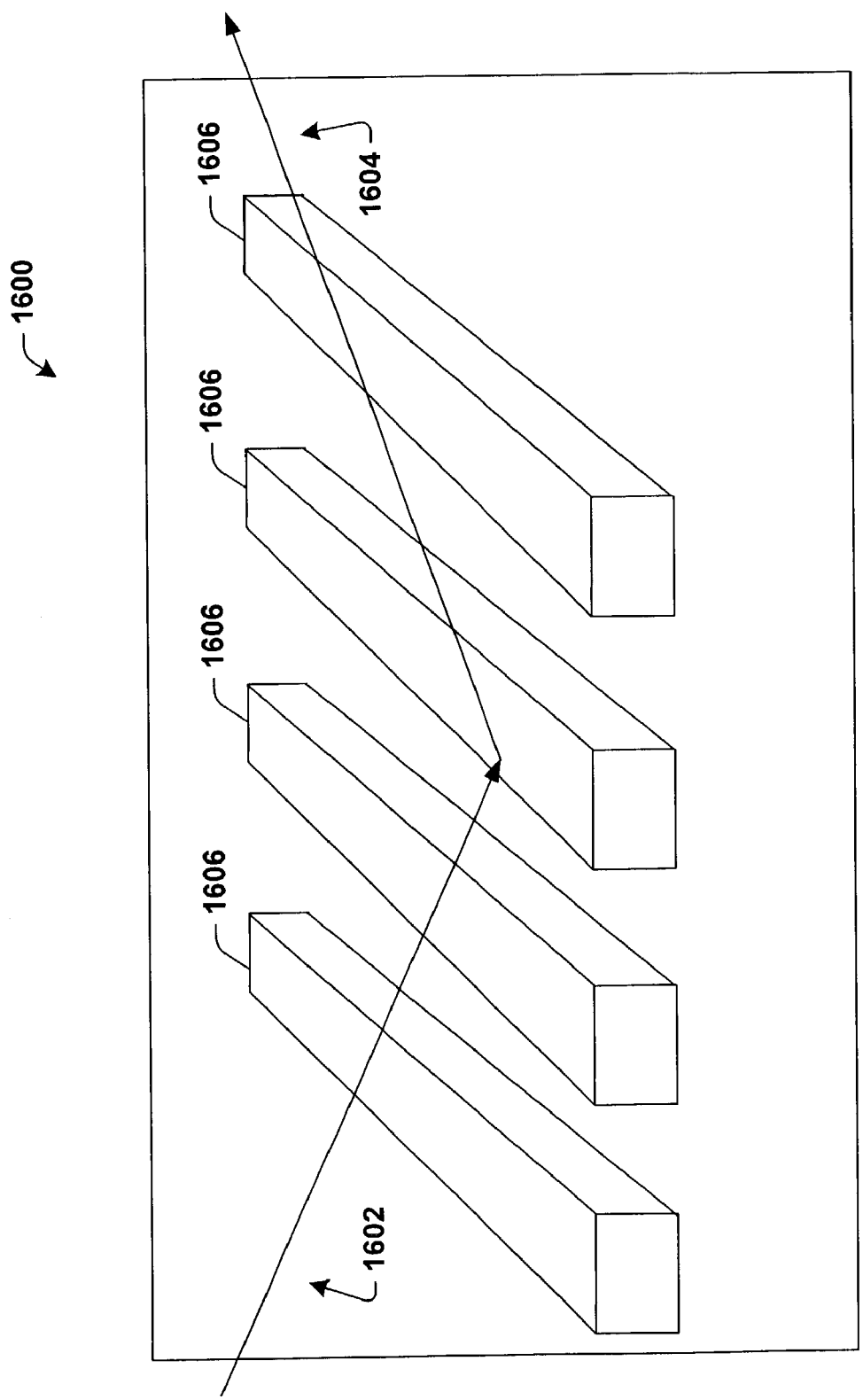
FIG. 16 is a simplified perspective view of an incident light reflecting off a surface in accordance with one or more aspects of the present invention.

To illustrate the principles described above, reference is now made to FIGS. 16 through 21. Referring initially to FIG. 16, an incident light 1602 is directed at a surface 1600, upon which one or more features 1606 may exist. The incident light 1602 is reflected as reflected light 1604. The properties of the surface 16, including but not limited to, thickness, uniformity, planarity, chemical composition and the presence of features, can affect the reflected light 1604. The features 1606 are raised upon the surface 1600, but could also be recessed therein. The phase and/or intensity of the reflected light 1604 can be measured and plotted, as partially shown, for example, in FIG. 21. Such plots can be employed to compare measured signals with signatures stored in a signature library using techniques like pattern matching, for example.

Figure 17:
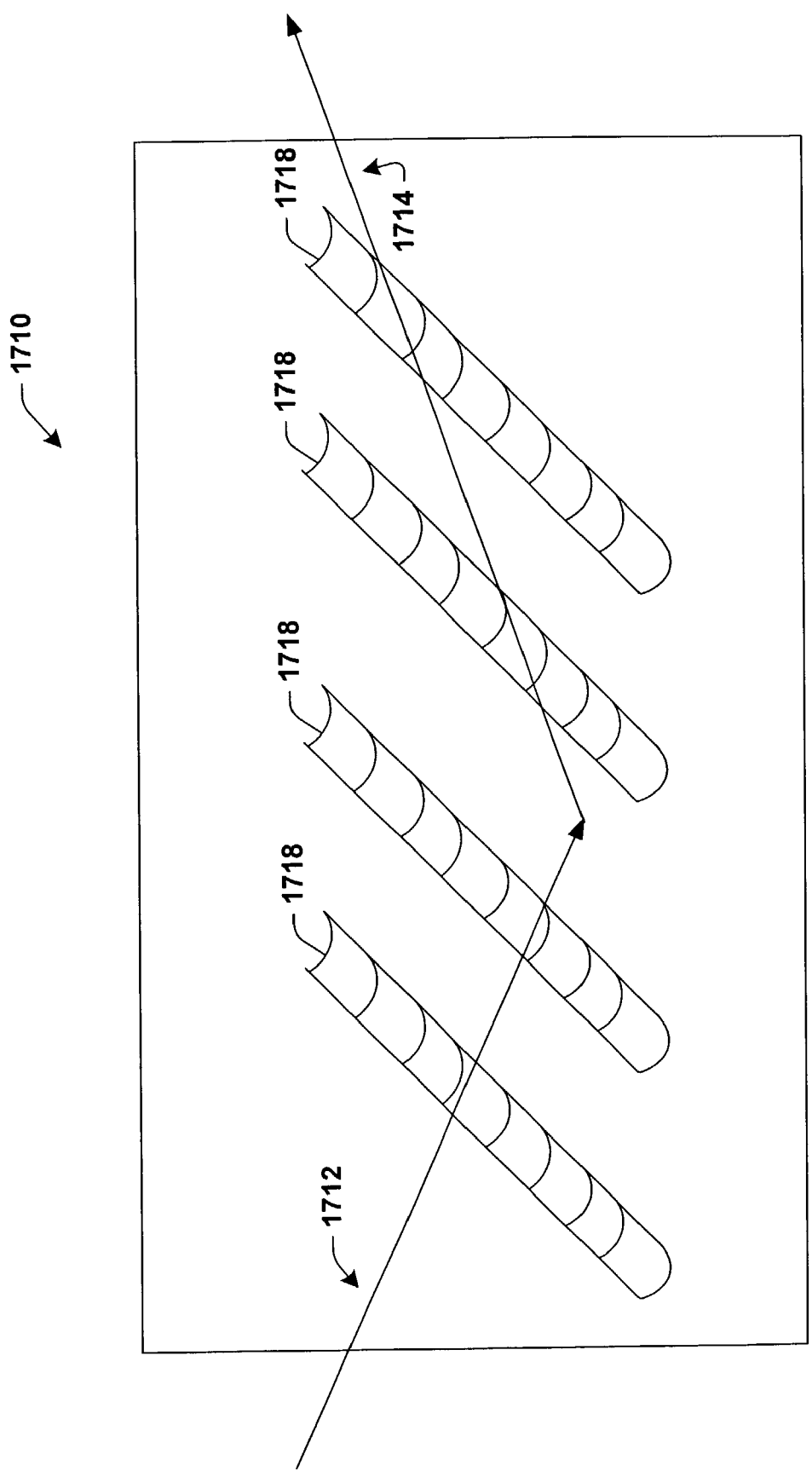
FIG. 17 is another simplified perspective view of an incident light reflecting off a surface in accordance with one or more aspects of the present invention.

Referring now to FIG. 17, an incident light 1712 is directed onto a surface 1710 upon which one or more depressions 1718 appear. The incident light 1712 is reflected as reflected light 1714. Depressions 1718 will affect the scatterometry signature to produce a substantially unique signature. It is to be appreciated that scatterometry can be employed to measure, among other things, features appearing on a surface, features appearing in a surface, features emerging in a pattern.

Figure 18:
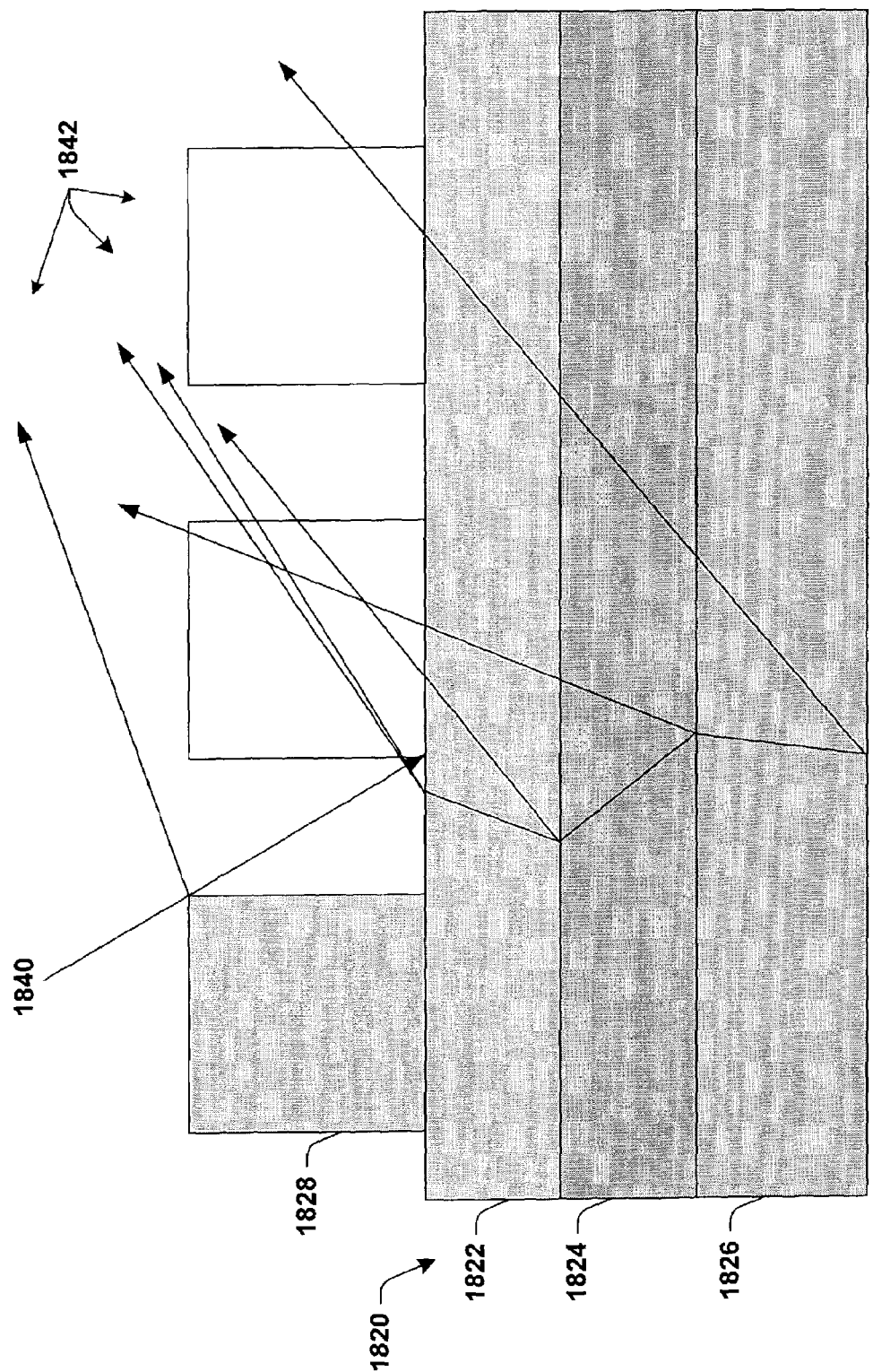
FIG. 18 illustrates a complex reflected and refracted light produced when an incident light is directed onto a surface in accordance with one or more aspects of the present invention.

Turning now to FIG. 18, complex reflections and refractions of an incident light 1840 are illustrated. The reflection and refraction of the incident light 1840 can be affected by factors including, but not limited to, the presence of one or more features 1828 and the composition of the substrate 1820 upon which the features 1828 reside. For example, properties of the substrate 1820 including, but not limited to the thickness of a layer 1822, the chemical properties of the layer 1822, the opacity and/or reflectivity of the layer 1822, the thickness of a layer 1824, the chemical properties of the layer 1824, the opacity and/or reflectivity of the layer 1824, the thickness of a layer 1826, the chemical properties of the layer 1826, and the opacity and/or reflectivity of the layer 1826 can affect the reflection and/or refraction of the incident light 1840. Thus, a complex reflected and/or refracted light 1842 may result from the incident light 1840 interacting with the features 1828, and/or the layers 1822, 1824 and 1826. Although three layers 1822, 1824 and 1826 are illustrated in FIG. 18, it is to be appreciated that a substrate can be formed of a greater or lesser number of such layers.

Figure 19:
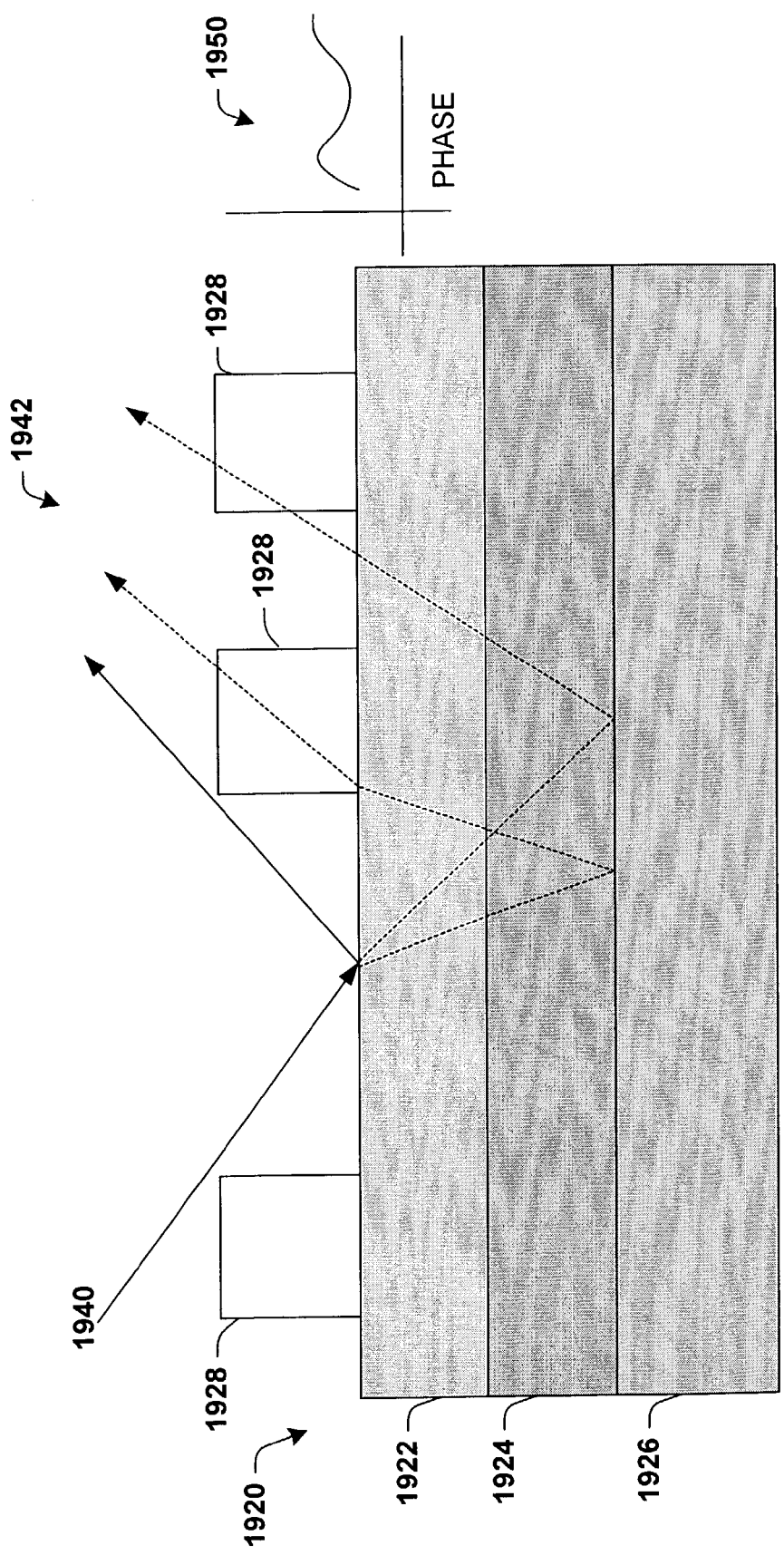
FIG. 19 illustrates another complex reflected and refracted light produced when an incident light is directed onto a surface in accordance with one or more aspects of the present invention.
Figure 20:
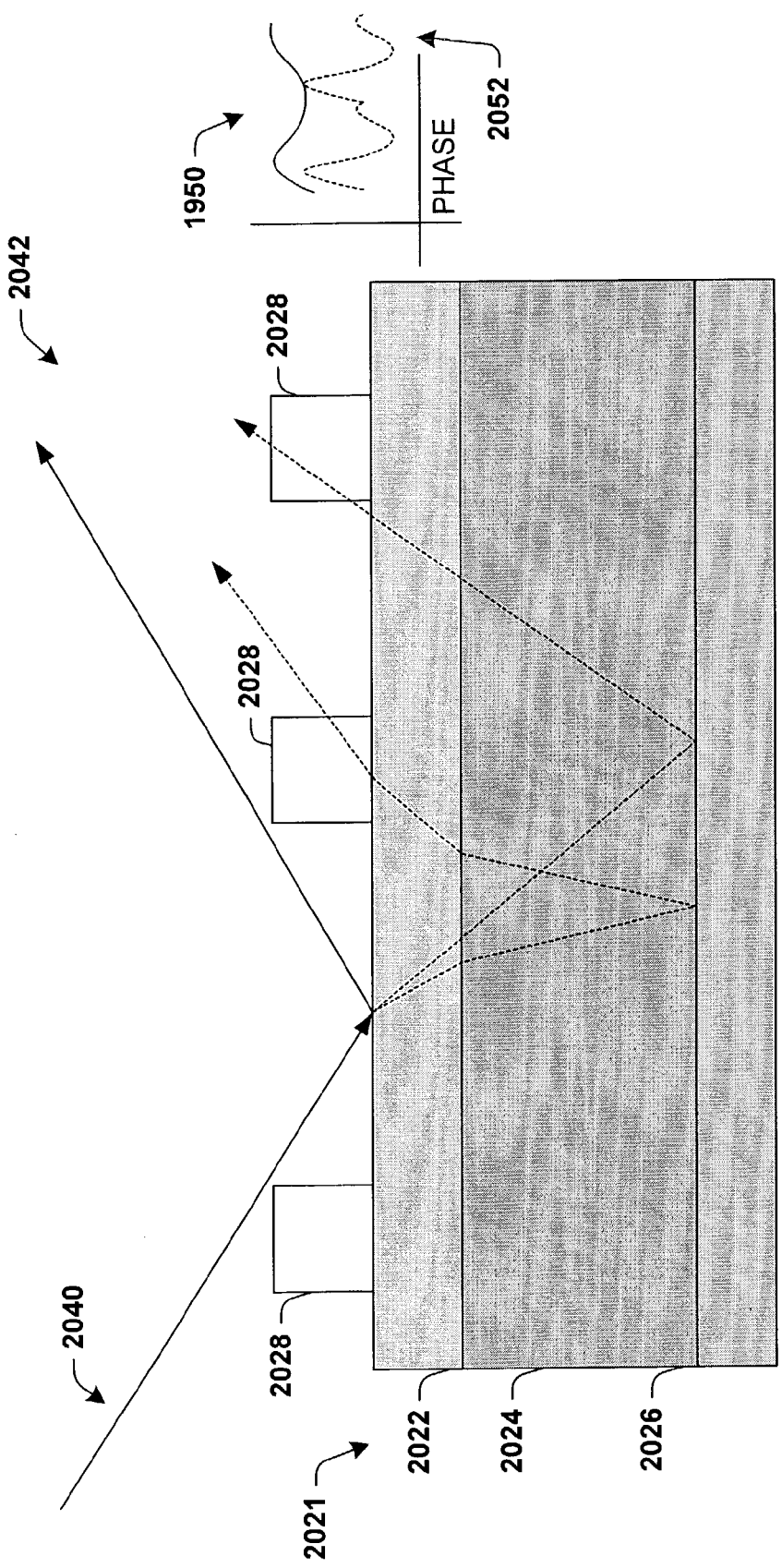
FIG. 20 illustrates yet another complex reflected and refracted light produced when an incident light is directed onto a surface in accordance with one or more aspects of the present invention.
Figure 21:
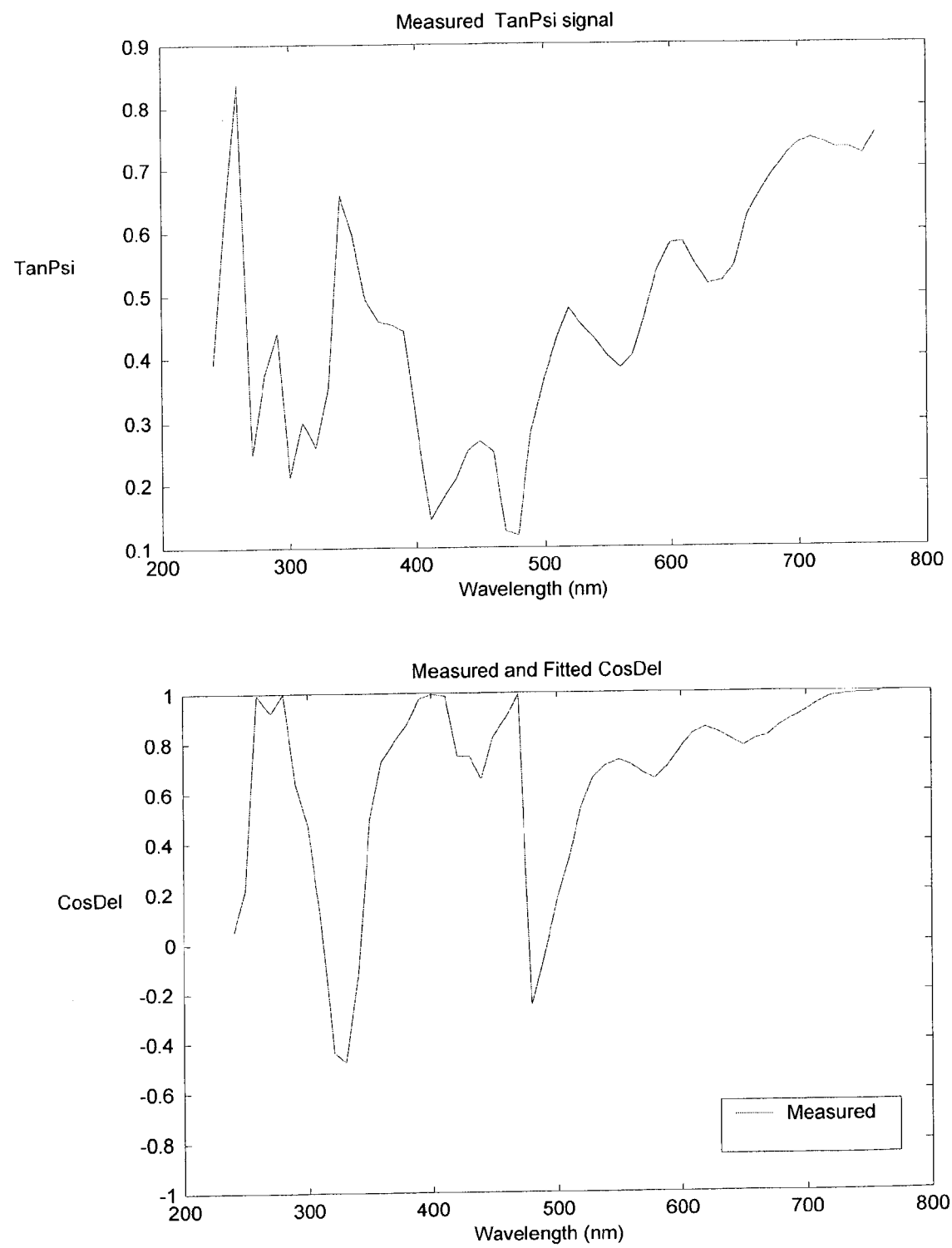
FIG. 21 illustrates phase and/or intensity signals recorded from a complex reflected and refracted light produced when an incident light is directed onto a surface in accordance with one or more aspects of the present invention.

Turning now to FIG. 19, one of the properties from FIG. 18 is illustrated in greater detail. The substrate 1920 can be formed of one or more layers 1922, 1924 and 1926. The phase 1950 of the reflected and/or refracted light 1942 from incident light 1940 can depend, at least in part, on the thickness of a layer, for example, the layer 1924. Thus, in FIG. 20, the phase 2052 of the reflected light 2042 differs from the phase 1950 due, at least in part, to the different thickness of the layer 2024 in FIG. 20.

Thus, scatterometry is a technique that can be employed to extract information about a surface upon which an incident light has been directed. The information can be extracted by analyzing phase and/or intensity signals of a complex reflected and/or diffracted light. The intensity and/or the phase of the reflected and/or diffracted light will change based on properties of the surface upon which the light is directed, resulting in substantially unique signatures that can be analyzed to determine one or more properties of the surface upon which the incident light was directed.

Using scatterometry in implementing one or more aspects of the present invention facilitates a relatively non-invasive approach to measuring opaque film thickness and other properties (e.g., CD, overlay, profile, etc.) and to reproducing successful fabrication processes in subsequent development cycles.

Described above are preferred embodiments of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A system that monitors and controls a semiconductor fabrication process comprising:
a structure formed on at least a portion of a wafer matriculating through the fabrication process that facilitates concurrent measurement of one or more critical dimensions and overlay,
a measurement system that concurrently measures one or more critical dimensions and overlay by mapping the wafer into one or more grids that comprises one or more locations on which a grating structure is formed; and
a control system operatively coupled to the measurement system and one or more fabrication components to selectively control one or more of the fabrication components or operating parameters of the fabrication components to mitigate overlay error and to bring critical dimensions within acceptable tolerances based upon one or more of the concurrent measurements taken by the measurement system.

2. The system of claim 1 wherein the structure, to facilitate concurrent measurement of one or more critical dimensions and overlay via scatterometry, comprises one or more underlying gratings that facilitate overlay measurements and one or more overlying gratings that facilitate critical dimension measurements.

3. The system of claim 2 wherein the overlying gratings comprise elongated raised portions.

4. The system of claim 2 wherein a first grouping of the overlying gratings comprises multiple elongated portions oriented substantially in parallel with one another to facilitate measuring overlay in a first direction.

5. The system of claim 2 wherein a second grouping of the overlying gratings comprises multiple elongated portions substantially in parallel with one another and oriented substantially perpendicular to the first grouping to facilitate measuring overlay in a second direction.

6. The system of claim 1 wherein the structure, to facilitate concurrent measurement of one or more critical dimensions and overlay via SEM, comprises one or more gratings formed in a material layer of the structure and one or more features formed within a resist layer of the structure, the material layer comprising at least one of polysilicon, nitride, and silicon dioxide.

7. The system of claim 6 wherein the SEM can interrogate the features for critical dimensions and portions of the gratings extending from the features for a determination of at least one of overlay and overlay error.

8. The system of claim 6 wherein the structure is formed within an implant layer of a flash memory product.

9. The system of claim 6 wherein the measurement system comprises:
a beam generating system from which an electron beam is generated and projected through an electromagnetic lens onto the structure; and
one or more detectors that detect electrons reflected off of the structure.

10. The system of claim 1 wherein the measurement system includes one or more light sources that direct light incident to the gratings; and
one or more light detecting components that collect light emitted from the gratings, the emitted light varying in at least one of angle, intensity, phase and polarization as the fabrication process progresses.

11. The system of claim 10 wherein the emitted light can be analyzed to generate one or more signatures for comparison to one or more stored signatures to determine whether one or more critical dimensions fall outside of acceptable tolerances and/or whether overlay error is occurring.

12. The system of claim 10 wherein the emitted light can be analyzed by an algorithm to obtain a measurement in order to determine whether one or more critical dimensions fall outside of acceptable tolerances and/or whether overlay error is occurring.

13. The system of claim 1 wherein the control system controls at least one of alignment, exposure, post exposure baking, development, photolithography, etching, polishing, deposition, exposure time, exposure intensity, exposure magnification, exposure de-magnification, movement via a stepper motor, temperatures associated with the process, pressures associated with the process, concentration of gases applied to the process, concentration of chemicals applied to the process, flow rates of gases applied to the process, flow rates of chemicals applied to the process, excitation voltages associated with the process, illumination time, illumination intensity, concentration of slurry applied during CMP, rate of flow of slurry applied during CMP, degree of abrasiveness of slurry applied during CMP, pressure applied during CMP, baking time, balking temperatures and etchant concentrations.

14. A system that facilitates concurrent measurement of one or more critical dimensions and overlay during a semiconductor fabrication process via scatterometry comprising;
one or more underlying gratings formed within an underlying layer of at least a portion of a wafer undergoing the semiconductor fabrication process that facilitates measurement of overlay by analyzing light reflected from the gratings;
one or more overlying gratings formed over the underlying gratings on an overlying layer of at least a portion of the wafer that facilitates measurement of one or more critical dimensions by analyzing reflected electrons; and
one or more logical grids mapped to the wafer comprising one or more locations in which the underlying and overlying gratings for use in concurrent measurements is formed.

15. The system of claim 14 wherein the overlying gratings comprise elongated raised portions.

16. The system of claim 14 wherein a first grouping of overlying gratings comprises multiple elongated portions oriented substantially in parallel with one another to facilitate measuring overlay in a first direction.

17. The system of claim 14 wherein a second grouping of overlying gratings comprises multiple elongated portions substantially in parallel with one another and oriented substantially perpendicular to the first grouping to facilitate measuring overlay in a second direction.

18. A system that facilitates concurrent measurement of one or more critical dimensions and overlay error during a semiconductor fabrication process via a scanning electron microscope (SEM) comprising:
one or more features formed in a resist layer of at least a portion of a wafer undergoing the fabrication process that facilitates measurement of one or more critical dimensions by analyzing electrons from an electron beam directed at and reflected from at least the portion of the wafer; and
one or more gratings formed under the features in a polysilicon layer of at least a portion of the wafer by mapping the wafer into one or more blocks comprising one or more locations in which the one or more gratings for use in the concurrent measurement is formed, portions of the gratings extending out from tinder the features facilitating a determination of overlay error by analyzing reflected electrons, the features are formed within an implant layer of a flash memory product.

19. A method for monitoring and controlling a semiconductor fabrication process comprising:
providing a plurality of wafers undergoing the fabrication process;
mapping the plurality of wafers into one or more logical grids comprising one or more portions in which a grating structure for use in concurrent measurements is formed;
concurrently measuring one or more critical dimensions and overlay in a wafer undergoing the fabrication process;
determining if one or more of the critical dimensions are outside of acceptable tolerances;
determining whether an overlay error is occurring;
developing control data based upon one or more concurrent measurements when at least one of an overlay error is occurring and one or more of the critical dimensions fall outside of acceptable tolerances; and
feeding forward or backward the control data to adjust one or more fabrication components or one or more operating parameters associated with the fabrication components when at least one of an overlay error is occurring and one or more of the critical dimensions fall outside of acceptable tolerances to mitigate overlay error and/or to bring critical dimension within acceptable tolerances.

20. The method of claim 19 further comprising:
forming at least one grating structure on at least a portion of the wafer that facilitates concurrent measurements of one or more critical dimensions and overlay using at least one of scatterometry and scanning electron microscope (SEM) techniques.

21. The method of claim 19 wherein scatterometry is utilized to concurrently measure one or more critical dimensions and overlay, the method further comprising:
forming one or more underlying gratings within an underlying layer of at least a portion of the wafer that facilitates measurement of overlay by reflecting light directed incident to the gratings; and
forming one or more overlying gratings over the underlying gratings on an overlying layer of at least a portion of the wafer that facilitates measurement of one or more critical dimensions by reflecting the incident light.

22. The method of claim 19 wherein SEM is utilized to concurrently measure one or more critical dimensions and overlay, the method further comprising:
forming one or more features in a resist layer of at least a portion of the wafer that facilitates measurement of one or more critical dimensions by analyzing electrons emitted from an electron beam directed at and reflected from at least the portion of the wafer; and
forming one or more gratings under the features in a polysilicon layer of at least a portion of the wafer, portions of the gratings extending out from under the features facilitating a determination of overlay error by analyzing the reflected electrons.

23. A system that monitors and controls a semiconductor fabrication process comprising:
means for mapping one or more logical grid blocks to at least one wafer;
means for forming at least one grain structure according to the one or more logical grid blocks associated with at least a portion of the wafer undergoing the fabrication process that facilitates concurrent measurements of one or more critical dimensions and overlay;
means for directing at least one of light and electrons onto the structure;
means for collecting light reflected from the structure;
means for analyzing the reflected light to determine whether at least one of an overlay error is occurring and one or more critical dimensions full outside of acceptable tolerances; and
means for adjusting one or more fabrication components or one or more operating parameters associated with the fabrication components when at least one of overlay error is occurring and one or more of the critical dimensions fall outside of acceptable tolerances to mitigate overlay error and/or to bring critical dimension within acceptable tolerances.

24. The system of claim 23 wherein the concurrent measurements are performed using at least one of scatterometry and SEM.

25. The system of claim 23 further comprising means for developing control data based upon one or more of the concurrent measurements when at least one of an overlay error is occurring and one or more of the critical dimensions fall outside of acceptable tolerances.

* * * * *